United States Patent
Kato et al.

(10) Patent No.: US 10,149,655 B2
(45) Date of Patent: Dec. 11, 2018

(54) PHOTON COUNTING IMAGING APPARATUS AND X-RAY DETECTION APPARATUS

(71) Applicant: Toshiba Medical Systems Corporation, Otawara-shi (JP)

(72) Inventors: Tooru Kato, Nasushiobara (JP); Mikihito Hayashi, Otawara (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 206 days.

(21) Appl. No.: 15/353,339

(22) Filed: Nov. 16, 2016

(65) Prior Publication Data
US 2017/0150932 A1    Jun. 1, 2017

(30) Foreign Application Priority Data
Dec. 1, 2015    (JP) .................. 2015-234651

(51) Int. Cl.
*A61B 6/00*    (2006.01)
*A61B 6/03*    (2006.01)

(52) U.S. Cl.
CPC ............ *A61B 6/4241* (2013.01); *A61B 6/032* (2013.01); *A61B 6/4233* (2013.01)

(58) Field of Classification Search
CPC .................................................. A61B 6/4241
See application file for complete search history.

(56) References Cited

U.S. PATENT DOCUMENTS

| 2008/0245950 | A1 | 10/2008 | Nakaya |
| 2015/0327827 | A1 | 11/2015 | Teshigawara |
| 2015/0346354 | A1* | 12/2015 | Arakita ............... G01T 1/1606 378/19 |
| 2016/0011323 | A1 | 1/2016 | Sasaki et al. |

FOREIGN PATENT DOCUMENTS

| JP | 2008-256522 | 10/2008 |
| JP | 2014-176620 | 9/2014 |
| JP | 2014-241543 | 12/2014 |

OTHER PUBLICATIONS

"Si APD, MPPC", Opto-Semiconductor Handbook, Chapter 03, Hamamatsu, https://www.hamamatsu.com/resources/pdf/ssd/e03_handbook_si_apd_mppc.pdf, 25 pages.

* cited by examiner

Primary Examiner — Dani Fox
(74) Attorney, Agent, or Firm — Oblon, McClelland, Maier & Neustadt, L.L.P.

(57) ABSTRACT

According to one embodiment, a photon counting imaging apparatus includes an X-ray tube, an X-ray detector, and data acquisition circuitry. The X-ray detector includes a detector pixel including photoelectric conversion cells each configured to individually generate an electrical signal of a predetermined pulse height, and output circuitry configured to generate an energy signal having a pulse height corresponding to energy of the X-rays based on the electrical signals from the photoelectric conversion cells. The data acquisition circuitry corrects the energy signal based on a relationship between an amplification factor and an applied voltage to the detector pixel during a period until the voltage applied to the detector pixel recovers from a breakdown voltage to a reverse bias voltage.

7 Claims, 14 Drawing Sheets

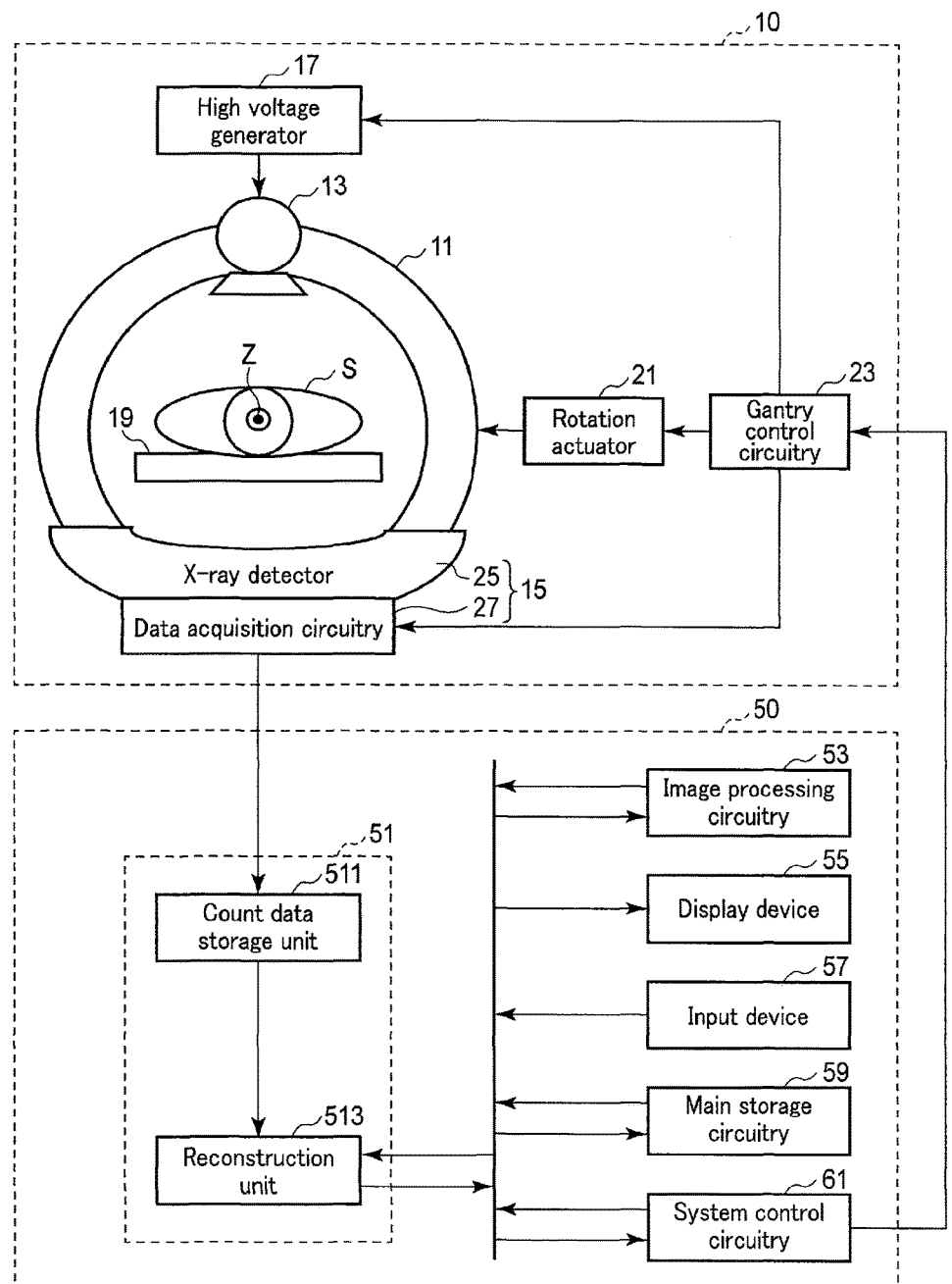
F I G. 1

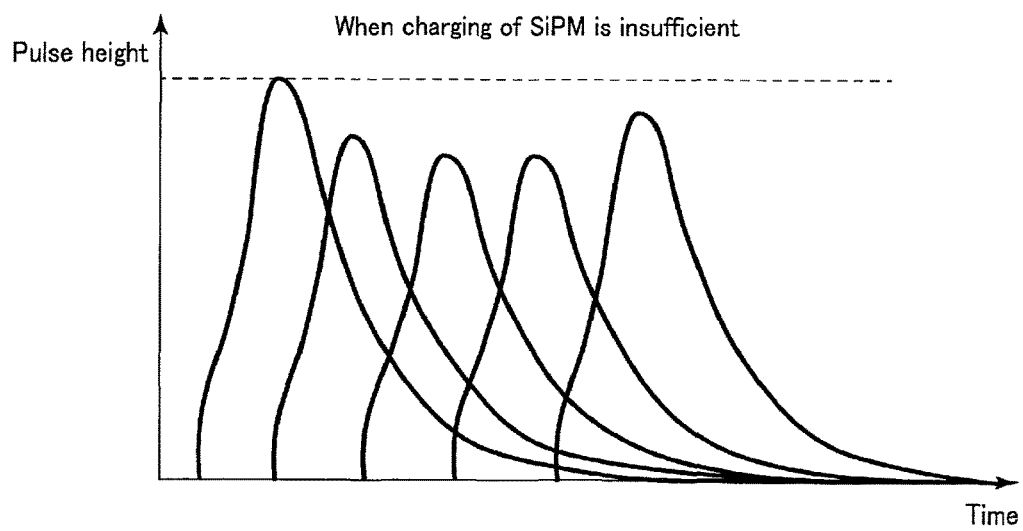
F I G. 7

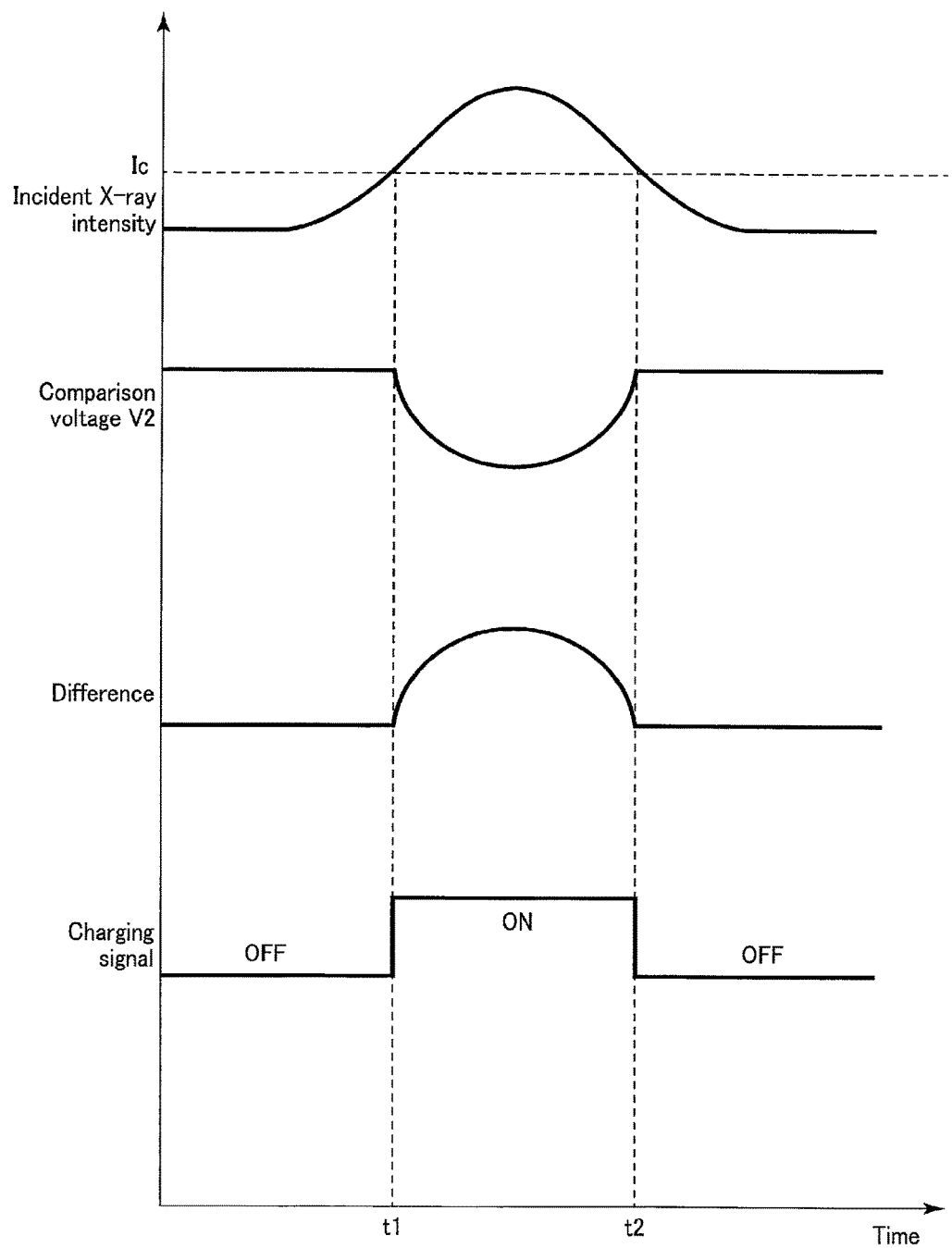
F I G. 9

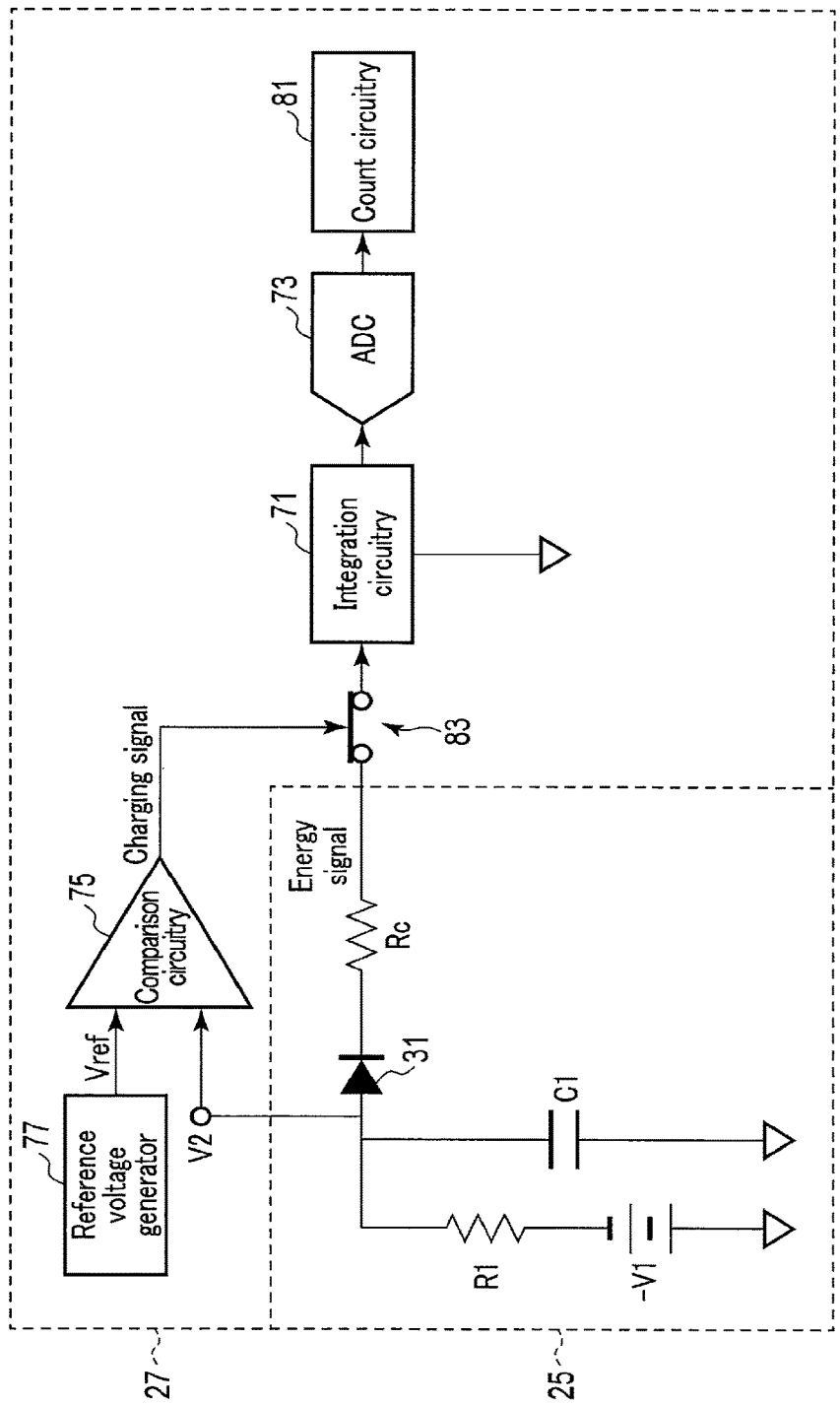
F I G. 10

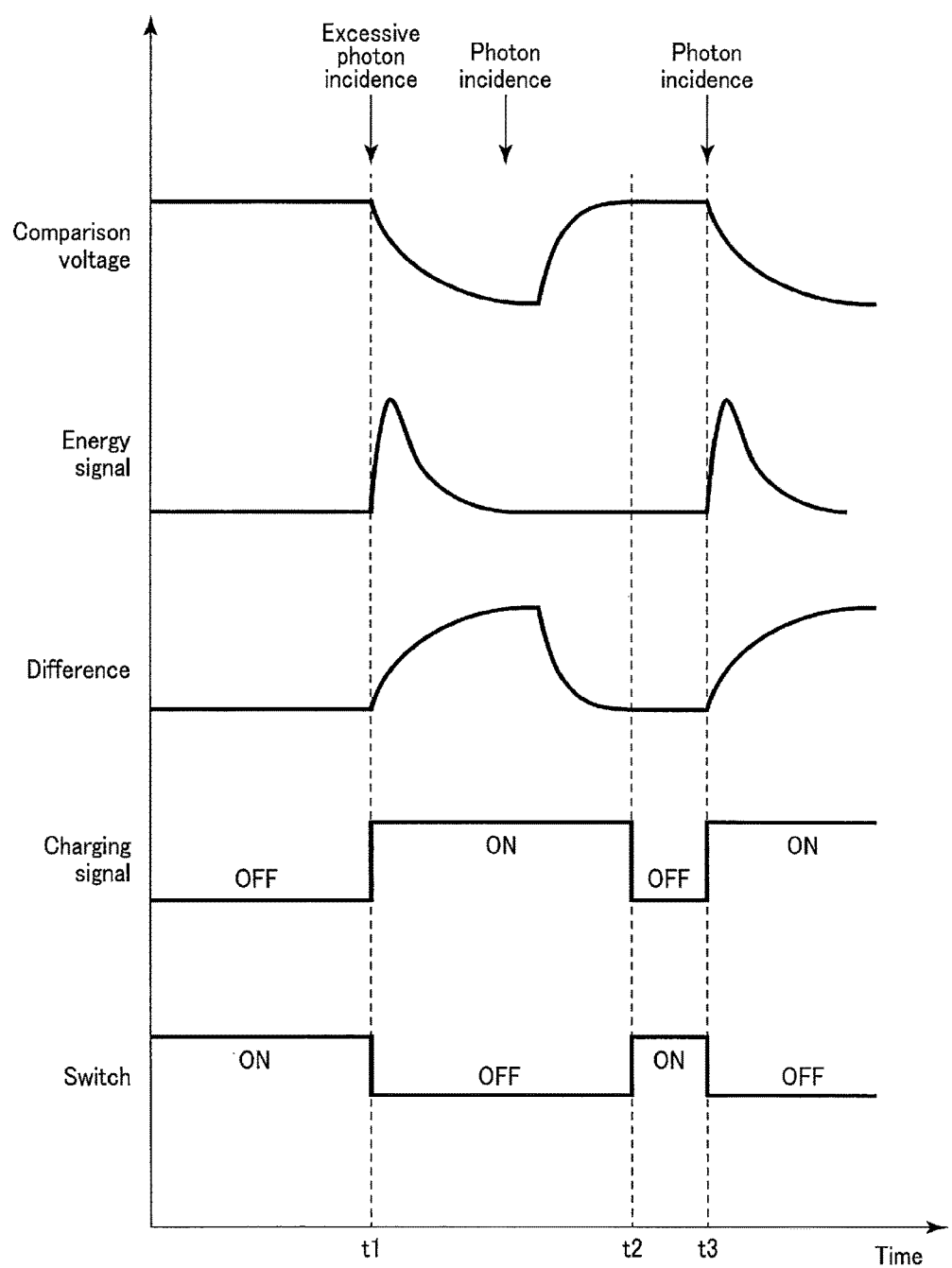
F I G. 11

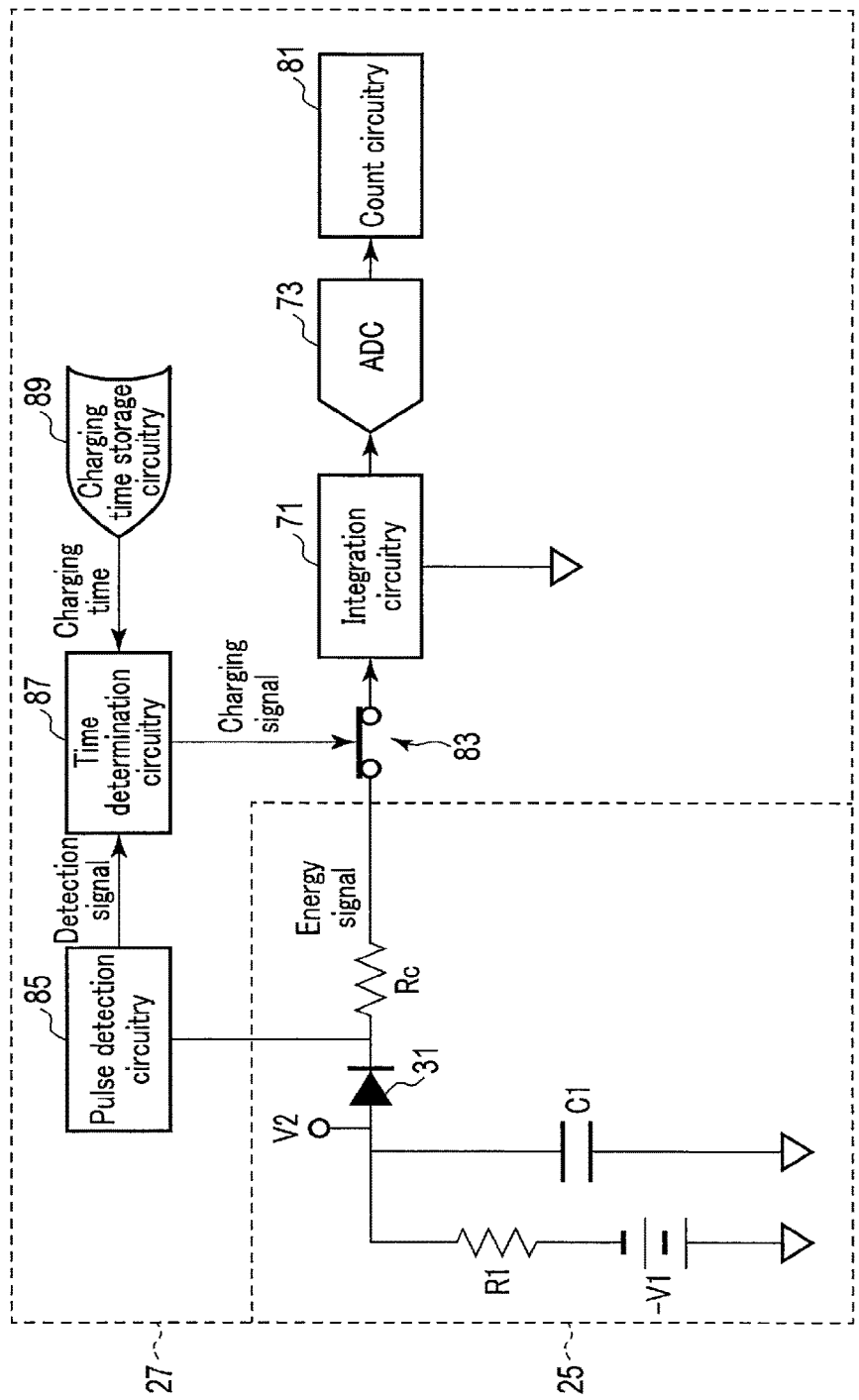
F I G. 12

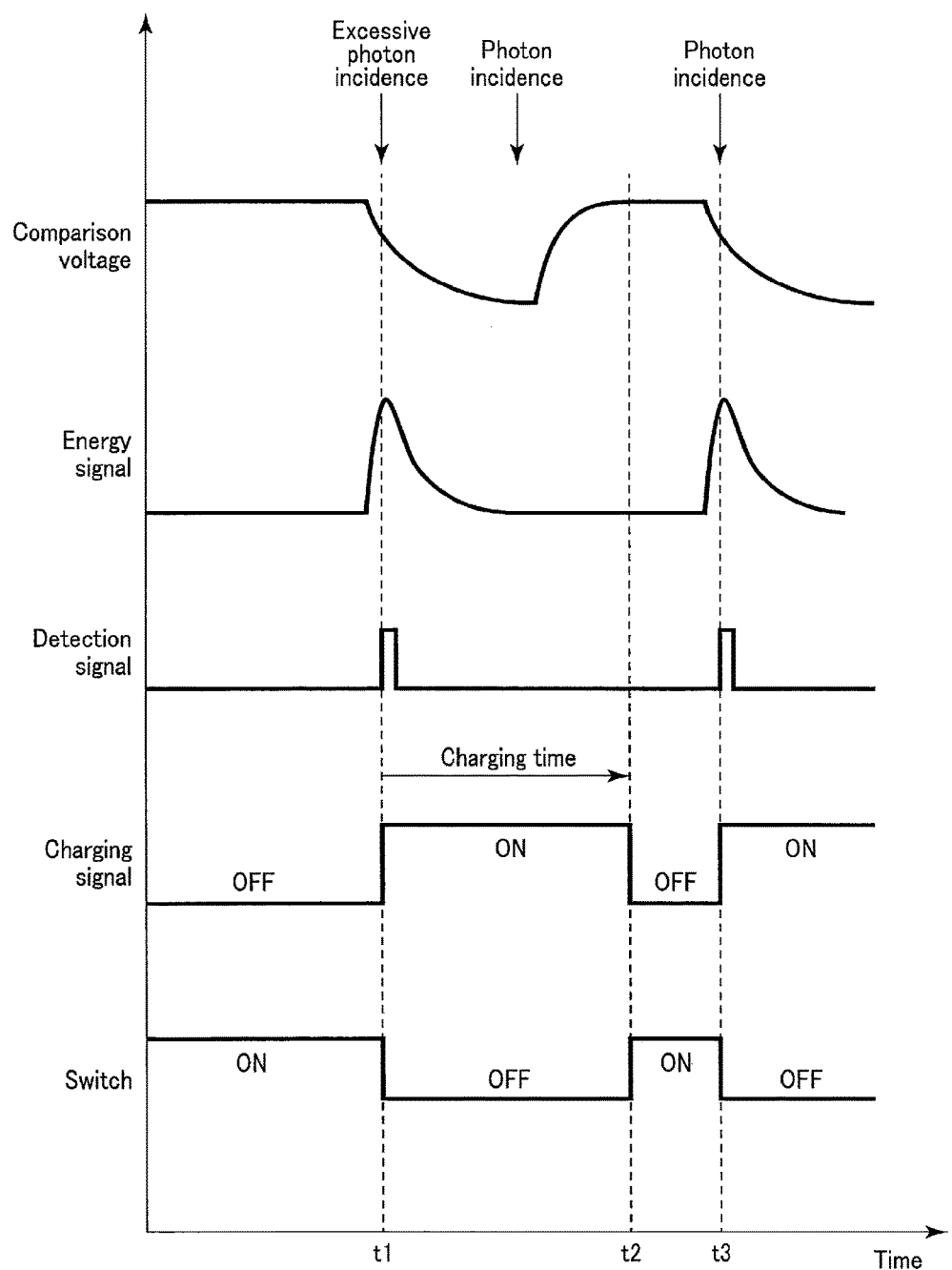
F I G. 13

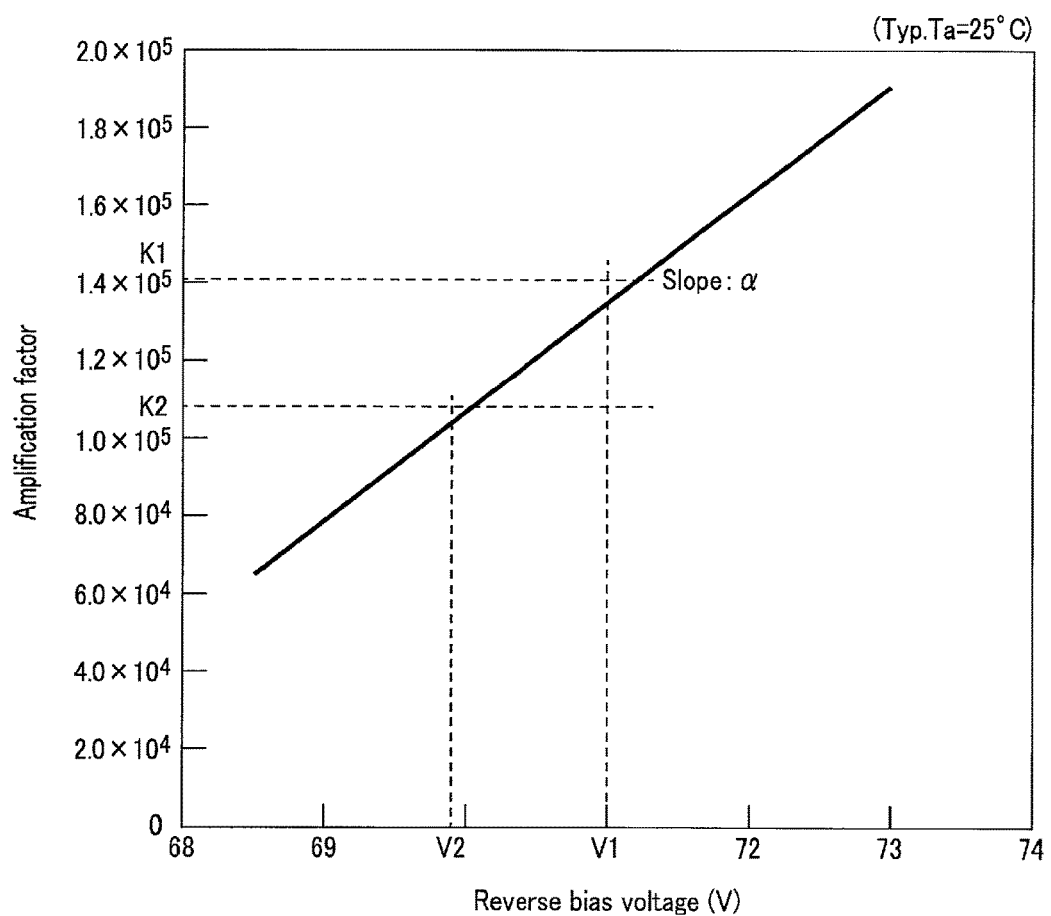
F I G. 15

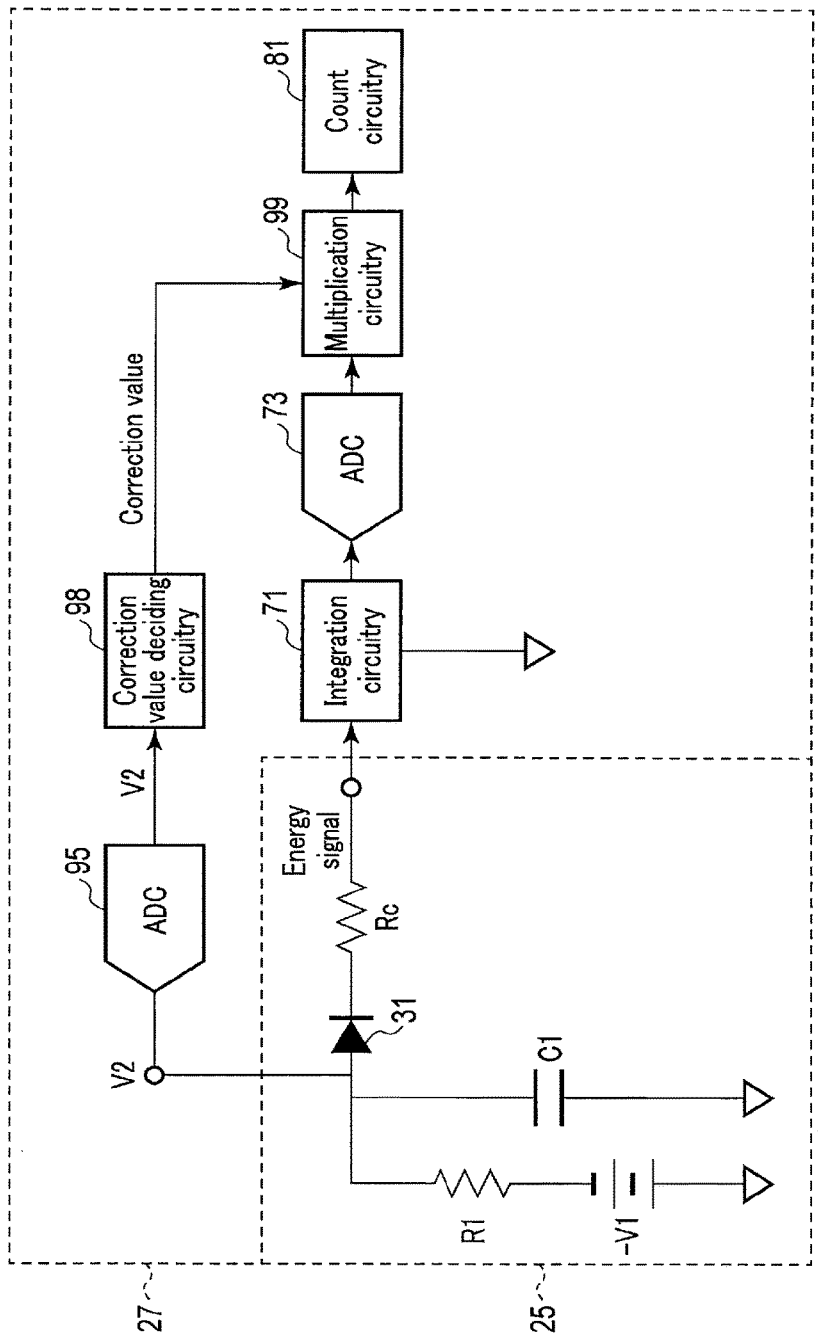
F I G. 16

PHOTON COUNTING IMAGING APPARATUS AND X-RAY DETECTION APPARATUS

CROSS-REFERENCE TO RELATED APPLICATIONS

This application is based upon and claims the benefit of priority from the prior Japanese Patent Application No. 2015-234651, filed Dec. 1, 2015 the entire contents of which are incorporated herein by reference.

FIELD

Embodiments described herein relate generally to a photon counting imaging apparatus and an X-ray detection apparatus.

BACKGROUND

As an X-ray detection apparatus used in an X-ray computed tomography apparatus, a photon counting type X-ray detection apparatus for measuring the energy of X-rays is known. As a photon counting type X-ray detection apparatus, there is an SiPM (Silicon Photo-Multiplier). The SiPM includes a plurality of detector pixels. Each detector pixel includes a scintillator and a plurality of APD (Avalanche Photo-Diode) cells. The scintillator converts incident X-rays into a plurality of scintillation photons. The plurality of scintillation photons are received by the plurality of APD cells. In a Geiger mode, each APD cell causes an electron avalanche (ignites) in response to one or more scintillation photons to generate a current pulse of a predetermined pulse height or charge amount independent of the number of scintillation photons. The number of APD cells that ignite depends on the number of scintillation photons (that is, the energy of the incident X-rays). A plurality of current pulses from the plurality of APD cells are integrated into one current pulse (output pulse). When the pulse height or charge amount of the output pulse is measured, the energy of the incident X-rays can be measured.

When the APD cells ignite in response to the scintillation photons, they need to be charged to be ignitable again. If the dose of X-rays that enter the SiPM is excessive, charging of the APD cells delays. If the insufficiently charged APD cells ignite, the apparent pulse height of the output pulse lowers. If this phenomenon occurs, it is impossible to make discrimination between a pulse height caused by undercharging and a truly low pulse height. The pulse height of the output pulse is an important physical quantity that decides the energy of X-rays. For this reason, it can be said that an X-ray detection apparatus that can cause lowering of a pulse height due to undercharging is not very reliable in terms of the accuracy of energy resolution.

BRIEF DESCRIPTION OF THE DRAWING

FIG. 1 is a view showing the arrangement of a photon counting CT apparatus according to the embodiment;

FIG. 7 is a graph showing the pulse height of a current pulse output from the detector pixel (SiPM) under a high dose;

FIG. 9 is a timing chart of the X-ray detection apparatus according to Example 1;

FIG. 10 is a block diagram showing the circuit arrangement of an X-ray detection apparatus according to Example 2 of the embodiment;

FIG. 11 is a timing chart of the X-ray detection apparatus according to Example 2;

FIG. 12 is a block diagram showing the circuit arrangement of an X-ray detection apparatus according to Example 3 of the embodiment;

FIG. 13 is a timing chart of the X-ray detection apparatus according to Example 3;

FIG. 15 is a graph showing the linear relationship between a reverse bias voltage and the amplification factor of a detector pixel according to Example 4; and FIG. 16 is a block diagram showing the circuit arrangement of an X-ray detection apparatus according to Example 5 of the embodiment.

DETAILED DESCRIPTION

Figure 2:
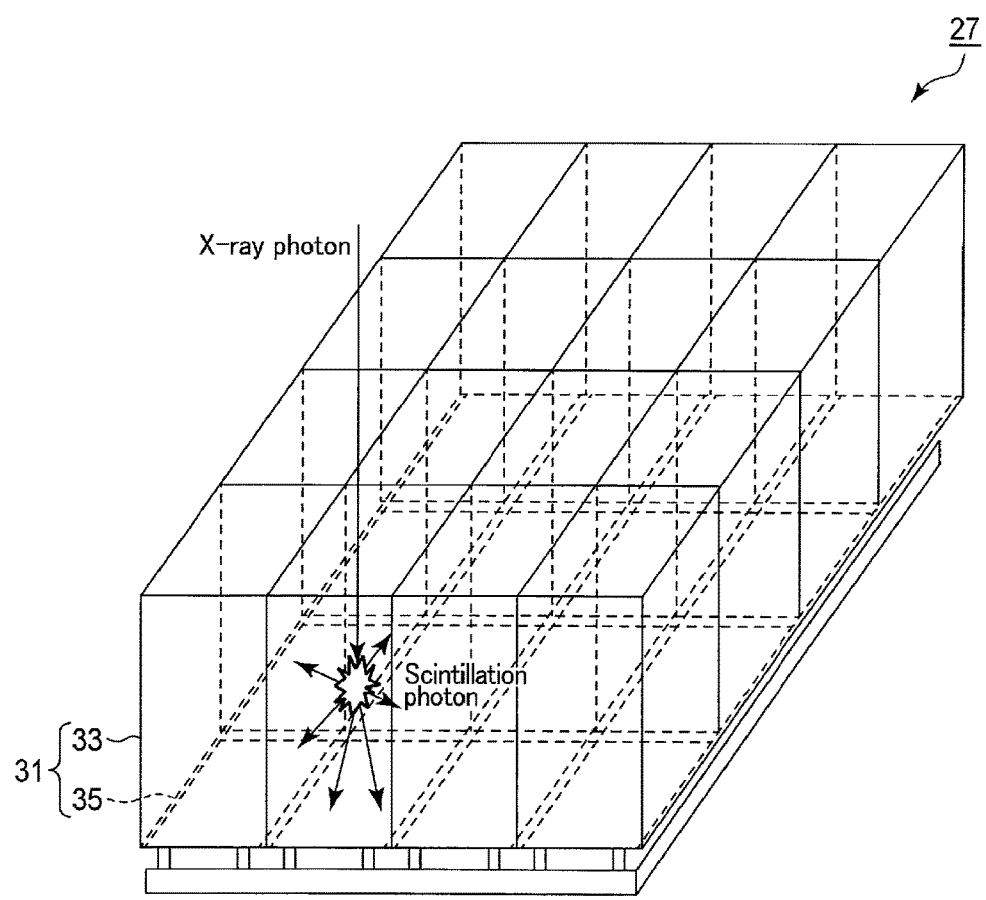
FIG. 2 is a schematic perspective view of a plurality of detector pixels (SiPMs) included in an X-ray detector shown in FIG. 1.

A photon counting imaging apparatus according to the embodiment includes an X-ray tube, an X-ray detector, and data acquisition circuitry. The X-ray tube generates X-rays. The X-ray detector includes a phosphor configured to convert the X-rays generated by the X-ray tube into scintillation, a detector pixel including a plurality of photoelectric conversion cells each configured to individually generate an electrical signal of a predetermined pulse height in response to the scintillation, and output circuitry configured to generate an energy signal having a pulse height corresponding to energy of the X-rays based on the electrical signals from the plurality of photoelectric conversion cells. The data acquisition circuitry generates count data representing a count of the X-rays for each energy band based on the energy signal. The data acquisition circuitry corrects the energy signal based on a relationship between an amplification factor and an applied voltage to the detector pixel during a period until the voltage applied to the detector pixel recovers from a breakdown voltage to a reverse bias voltage.

A photon counting imaging apparatus and an X-ray detection apparatus according to the embodiment will now be described with reference to the accompanying drawings.

The photon counting imaging apparatus according to the embodiment is applicable to any one of an X-ray CT type apparatus (to be referred to as a photon counting CT apparatus hereinafter) and an X-ray radiology type apparatus (to be referred to as a photon counting XR apparatus hereinafter). The photon counting imaging apparatus according to the embodiment will be described below in detail using a photon counting CT apparatus as a detailed example.

Various types of photon counting CT apparatuses can be assumed, including a rotate/rotate-type apparatus in which an X-ray tube and an X-ray detection apparatus integrally rotate around a subject and a stationary/rotate-type apparatus in which a number of detector pixels arranged in a ring are fixed, and only an X-ray tube rotates around a subject. This embodiment is applicable to any type. However, in the following explanation, the photon counting CT apparatus is assumed to be a rotate/rotate-type apparatus.

FIG. 1 is a view showing the arrangement of the photon counting CT apparatus according to this embodiment. As shown in FIG. 1, the photon counting CT apparatus according to this embodiment includes a gantry 10 and a console 50. For example, the gantry 10 is placed in a CT examination room, and the console 50 is placed in a control room adjacent to the CT examination room. The gantry 10 and the console 50 are connected wirelessly or via a cable to be communicable with each other. The gantry 10 is a scanning apparatus having an arrangement for performing photon counting CT imaging of a subject S. The console 50 is a computer that controls the gantry 10.

The gantry 10 supports a rotation frame 11 with a cylindrical shape rotatably about a rotation axis Z. The rotation frame 11 is a metal frame made of a metal such as aluminum into an annular shape. An X-ray tube 13 and an X-ray detection apparatus 15 are attached to the rotation frame 11 to face each other across the rotation axis Z. More specifically, the gantry 10 has a main frame (not shown) made of a metal such as aluminum. The rotation frame 11 is supported by the main frame via a bearing and the like to be rotatable about the rotation axis Z. A slip ring (not shown) is provided on the contact portion of the main frame to the rotation frame 11. A conductive brash (not shown) is attached to the contact portion of the main frame to be in slidable contact with the slip ring. Power from a power supply unit (not shown) stored in the gantry 10 is supplied via the slip ring and the brash to various kinds of devices such as the X-ray detection apparatus 15 and a high voltage generator 17 mounded on the rotation frame 11.

An FOV (Field Of View) is set in the bore of the rotation frame 11. A top plate 19 is inserted into the bore of the rotation frame 11. The subject S is placed on the top plate 19. The top plate 19 is positioned such that the imaging portion of the subject S placed on the top plate 19 is included in the FOV. The rotation frame 11 rotates about the rotation axis Z at a predetermined angular velocity upon receiving power from a rotation actuator 21. As the rotation actuator 21, an arbitrary motor such as a direct drive motor or a servo motor is used. The rotation actuator 21 is stored in, for example, the gantry 10. Upon receiving a driving signal from gantry control circuitry 23, the rotation actuator 21 generates power to rotate the rotation frame 11.

The X-ray tube 13 is connected to the high voltage generator 17. The high voltage generator 17 is attached to, for example, the rotation frame 11. The high voltage generator 17 generates a high voltage to be applied to the X-ray tube 13 from the power supplied from the power supply unit (not shown) of the gantry 10 via the slip ring and the brash under the control of gantry control circuitry 23. The high voltage generator 17 and the X-ray tube 13 are connected via a high voltage cable (not shown). The high voltage generated by the high voltage generator 17 is applied to the X-ray tube 13 via the high voltage cable.

The X-ray detection apparatus 15 detects X-rays generated by the X-ray tube 13 on a photon basis. More specifically, the X-ray detection apparatus 15 includes an X-ray detector 25 and data acquisition circuitry 27. The X-ray detector 25 detects X-rays generated by the X-ray tube 13. More specifically, the X-ray detector 25 includes a plurality of detector pixels (not shown) arranged on a two-dimensional curved surface. Each detector pixel detects X-rays. As the X-ray detector 25 according to this embodiment, for example, an SiPM (Silicon Photo-Multiplier) is applied. More specifically, for each detector pixel, the SiPM type X-ray detector 25 includes a phosphor configured to convert X-rays generated by the X-ray tube 13 into scintillation, a plurality of photoelectric conversion cells each configured to individually generate an electrical signal of a predetermined pulse height in response to the scintillation, and output circuitry (not shown) configured to generate an output signal (to be referred to as an energy signal hereinafter) having a pulse height corresponding to the energy of the incident X-rays based on the electrical signals from the plurality of photoelectric conversion cells, as will be described later in detail. Based on the energy signal from the X-ray detector 25, the data acquisition circuitry 27 generates digital data (to be referred to as count data hereinafter) representing the count of X-rays detected by the X-ray detector 25 for each of a plurality of energy bands (energy bins). The data acquisition circuitry 27 is configured to be able to switch the count data generation mode between the charging period and the charging completion period of the plurality of photoelectric conversion cells included in the X-ray detector 25, as will be described later in detail. Count data is a set of the data of count values identified by the channel number and the row number of a detector pixel as a generation source of the count data, a view number representing an acquired view, and an energy bin number. The count data is supplied to the console 50 via, for example, a noncontact data transmission apparatus (not shown) stored in the gantry 10.

The gantry control circuitry 23 synchronously controls the X-ray detection apparatus 15, the high voltage generator 17, and the rotation actuator 21, and performs photon counting CT imaging of the subject S under the control of system control circuitry 61 in the console 50. The gantry control circuitry 23 includes, as hardware resources, a processing unit (processor) such as a CPU (Central Processing Unit) or an MPU (Micro Processing Unit) and storage devices (memories) such as a ROM (Read Only Memory) and a RAM (Random Access Memory). The gantry control circuitry 23 may be provided in the gantry 10 or the console 50, or in an apparatus separated from the gantry 10 and the console 50. The gantry control circuitry 23 may be implemented by an ASIC (Application Specific Integrated Circuit), an FPGA (Field Programmable Gate Array), a CPLD (Complex Programmable Logic Device), or an SPLD (Simple Programmable Logic Device). The processing unit implements the function by reading out a program saved in the storage device and executing it. Note that instead of saving the program in the storage device, the program may directly be embedded in circuitry of the processing unit. In this case, the processing unit implements the function by reading out the program embedded in the circuitry and executing it.

As shown in FIG. 1, the console 50 includes image reconstruction circuitry 51, image processing circuitry 53, a display device 55, an input device 57, main storage circuitry 59, and the system control circuitry 61 which are connected via a bus. Data communication between the image reconstruction circuitry 51, the image processing circuitry 53, the display device 55, the input device 57, the main storage circuitry 59, and the system control circuitry 61 is performed via the bus.

The image reconstruction circuitry 51 reconstructs an image concerning the subject S based on count data from the gantry 10. More specifically, the image reconstruction circuitry 51 includes count data storage circuitry 511 and a reconstruction unit 513. The count data storage circuitry 511 is a storage device that stores count data transmitted from the gantry 10, such as an HDD, an SSD, or an integrated circuit storage device. The reconstruction unit 513, for example, generates a photon counting CT image that expresses the spatial distribution of each base substance included in the subject S based on count data concerning a plurality of energy bins. As the image reconstruction algorithm, an existing image reconstruction algorithm, for example, an analytic image reconstruction method such as FBP (Filtered Back Projection) or CBP (Convolution Back Projection) or a statistical image reconstruction method such as ML-EM (Maximum Likelihood Expectation Maximization) or OS-EM (Ordered Subset Expectation Maximization) is used.

The image reconstruction circuitry 51 includes, as hardware resources, processing units (processors) such as a CPU or an MPU, and a GPU (Graphics Processing Unit) and storage devices (memories) such as a ROM and a RAM. The image reconstruction circuitry 51 may be implemented by an ASIC, an FPGA, a CPLD, an SPLD, or the like. The processing unit implements the function of the reconstruction unit 513 by reading out a program saved in the storage device and executing it. Note that instead of saving the program in the storage device, the program may directly be embedded in circuitry of the processing unit. In this case, the processing unit implements the function of the reconstruction unit 513 by reading out the program embedded in the circuitry and executing it. Alternatively, dedicated hardware circuitry that functions as the reconstruction unit 513 may be implemented in the image reconstruction circuitry.

The image processing circuitry 53 performs various kinds of image processing for the CT image reconstructed by the image reconstruction circuitry 51. For example, if the CT image is volume data, the image processing circuitry 53 performs three-dimensional image processing such as volume rendering, surface volume rendering, image value projection processing, MPR (Multi-Planer Reconstruction) processing, and CPR (Curved MPR) processing for the CT image to generate a display image. The image processing circuitry 53 includes, as hardware resources, processing units (processors) such as a CPU or an MPU, and a GPU and storage devices (memories) such as a ROM and a RAM. The image processing circuitry 53 may be implemented by an ASIC, an FPGA, a CPLD, an SPLD, or the like.

The display device 55 displays various kinds of information such as a two-dimensional CT image and a display image. As the display device 55, for example, a CRT display, a liquid crystal display, an organic EL display, an LED display, a plasma display, or another arbitrary display known in the technical field can appropriately be used.

The input device 57 accepts various kinds of instructions and information inputs from the user. As the input device 57, a keyboard, a mouse, various kinds of switches, or the like can be used. Note that the input device 57 may be provided in the console 50 or the gantry 10.

The main storage circuitry 59 is a storage device configured to store various kinds of information, such as an HDD, an SSD, or an integrated circuit storage device. The main storage circuitry 59 may be a driving unit or the like configured to read/write various kinds of information from/to a CD-ROM drive or a DVD drive, or a portable storage medium such as a flash memory. For example, the main storage circuitry 59 stores a control program and the like concerning photon counting CT imaging according to this embodiment.

The system control circuitry 61 includes, as hardware resources, a processing unit (processor) such as a CPU (Central Processing Unit) or an MPU (Micro Processing Unit) and storage devices (memories) such as a ROM (Read Only Memory) and a RAM (Random Access Memory). The system control circuitry 61 may be implemented by an ASIC, an FPGA, a CPLD, or an SPLD. The system control circuitry 61 functions as the core of the X-ray computed tomography imaging apparatus according to this embodiment. More specifically, the system control circuitry 61 reads out a control program stored in the main storage circuitry 59, loads it onto the memory, and controls the units of the X-ray computed tomography imaging apparatus in accordance with the loaded control program.

The image reconstruction circuitry 51, the image processing circuitry 53, and the system control circuitry 61 may be integrated on a single board in the console 50 or distributed to a plurality of boards.

Details of the photon counting CT apparatus according to this embodiment will be described below.

The X-ray detection apparatus according to this embodiment will be explained first.

FIG. 2 is a schematic perspective view of a plurality of detector pixels (SiPMs) included in the X-ray detector 25. As shown in FIG. 2, the X-ray detector 25 includes a plurality of detector pixels 31 two-dimensionally arranged on a semiconductor substrate. For example, 8,000 or more detector pixels 31 are arranged in one X-ray detector 25. More specifically, 500 channels of detector pixels are arranged in the channel direction, and 16 or more rows of detector pixels are arranged in the row direction. Each detector pixel 31 includes a phosphor 33 and a semiconductor chip 35. The phosphor 33 is called a scintillator. The plurality of phosphors 33 have, for example, a columnar shape each and are separated by a light-shielding member (not shown) from each other. Each scintillator 33 interacts with an X-ray photon from the X-ray tube 13, and converts the X-ray photon into a plurality of scintillation photons. As the scintillator 33, for example, an arbitrary crystal such as GSO or $LaBr_3$ is used.

Figure 3:
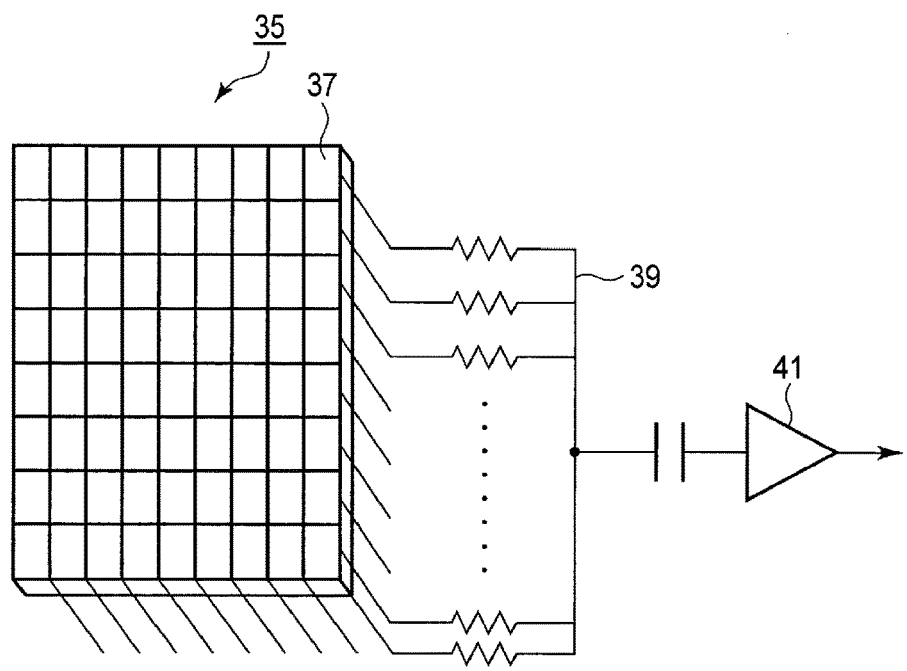
FIG. 3 is a schematic circuit diagram of a semiconductor chip shown in FIG. 2.

FIG. 3 is a schematic circuit diagram of the semiconductor chip 35. As shown in FIG. 3, a plurality of photoelectric conversion cells are implemented in each semiconductor chip 35. As the photoelectric conversion cell according to this embodiment, an APD (Avalanche Photo-Diode) cell is used. A plurality of APD cells 37 are two-dimensionally arranged on the semiconductor chip 35. From the viewpoint of an energy resolution and guaranteeing of a dynamic range, for example, several hundred to several thousand APD cells are arranged in one detector pixel 31. The APD cell 37 is made of a semiconductor based on silicon. As the structure of the APD cell 37, a reach through type or a reverse type is known. As the APD cell 37 according to this embodiment, any existing structure is usable.

Figure 4:
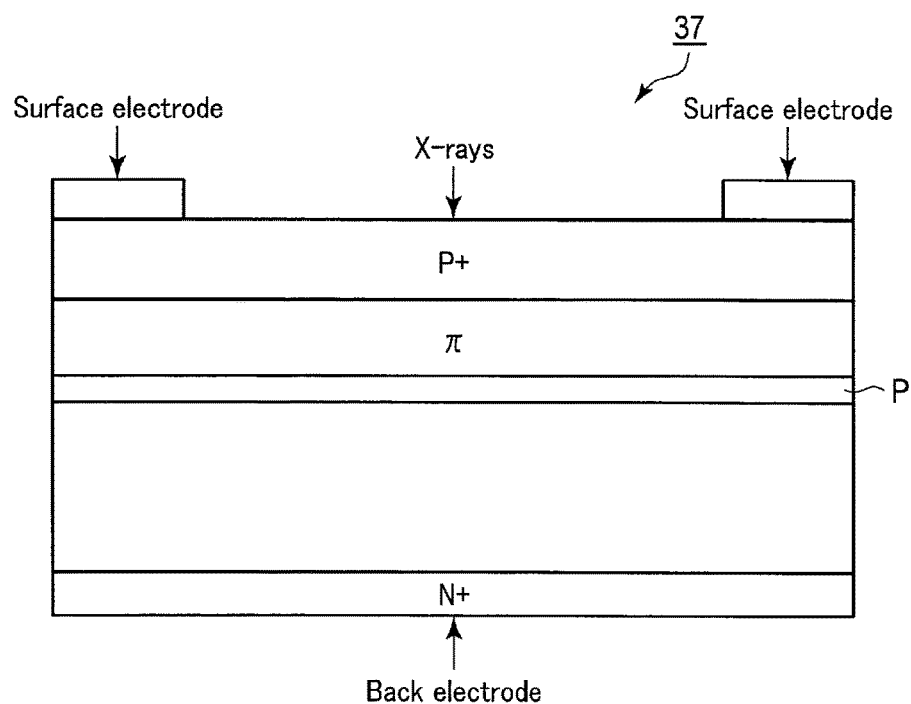
FIG. 4 is a view showing a schematic longitudinal section of an APD cell shown in FIG. 3.

FIG. 4 is a view showing a schematic longitudinal section of the APD cell 37. The APD cell 37 shown in FIG. 4 is, for example, an APD cell for a short wavelength. This embodiment is limited to this, and is applicable to various types such as an APD cell for infrared. The APD cell 37 explosively generates electron-hole pairs upon receiving scintillation photons from the scintillator 33. This phenomenon is called an electron avalanche. By the electron avalanche, the APD cell 37 generates a current pulse of a predetermined amount. The phenomenon that the APD cell 37 causes an electron avalanche is called "ignite".

The plurality of APD cells 37 included in the semiconductor chip 35 are connected to waveform shaping circuitry 41 via common output circuitry 39 shown in FIG. 3. The output circuitry 39 superimposes current pulses generated by the plurality of APD cells 37 to generate an energy signal that is a current pulse corresponding to the energy of X-ray photons that have entered the detector pixel 31. The waveform shaping circuitry 41 shapes the waveform of the energy signal from the output circuitry 39.

Figure 5:
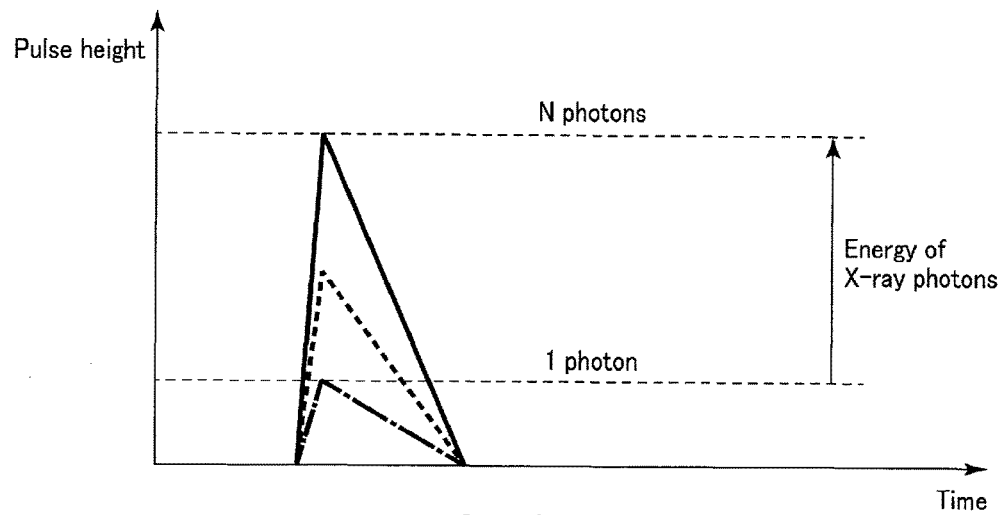
FIG. 5 is a graph schematically showing the pulse height of an energy signal output from the detector pixel shown in FIG. 3.

FIG. 5 is a graph schematically showing the pulse height of the energy signal output from the detector pixel 31. As described above, the number of scintillation photons generated by the scintillator 33 depends on the energy of incident X-ray photons. Each APD cell 37 outputs a current pulse having a predetermined pulse height independently of the energy of the X-ray photons. Hence, the pulse height of the energy signal that is the superimposition result of the current pulses output from the plurality of APD cells 37 belonging to each detector pixel 31 depends on the energy of the incident X-ray photons. When the pulse height of the energy signal is discriminated, the energy of the X-ray photons that have entered the detector pixel 31 can be discriminated.

The operation mode of the APD cell 37 is divided into a standard mode and a Geiger mode. The standard mode is an operation mode in a case in which a voltage equal to or lower than a breakdown voltage is applied to the APD cell 37. In this case, an electrical signal of a charge amount proportional to the number of scintillation photons that have entered the APD cell 37 is output from the APD cell 37. The Geiger mode is an operation mode in a case in which a voltage equal to or higher than a breakdown voltage is applied to the APD cell 37. In this case, as described above, a current pulse of a predetermined charge amount that depends on the voltage value but is irrelevant to the number of scintillation photons that have entered the APD cell 37 is output from the APD cell 37. When the current pulse is output from the APD cell 37, a current flows to a quenching resistor (not shown). During this time, the voltage value applied to the APD cell 37 lowers from the reverse bias voltage to the breakdown voltage. When the voltage value applied to the APD cell 37 lowers to the breakdown voltage, output of the current pulse from the APD cell 37 ends. When the voltage value applied to the APD cell 37 reaches the breakdown voltage, the APD cell 37 is recharged. By the recharging, the voltage applied to the APD cell 37 recovers from the breakdown voltage to the reverse bias voltage. The period when the voltage recovers from the breakdown voltage to the reverse bias voltage is called a charging period. When the voltage recovers to the reverse bias voltage, the Geiger mode operation can be performed again.

Figure 6:
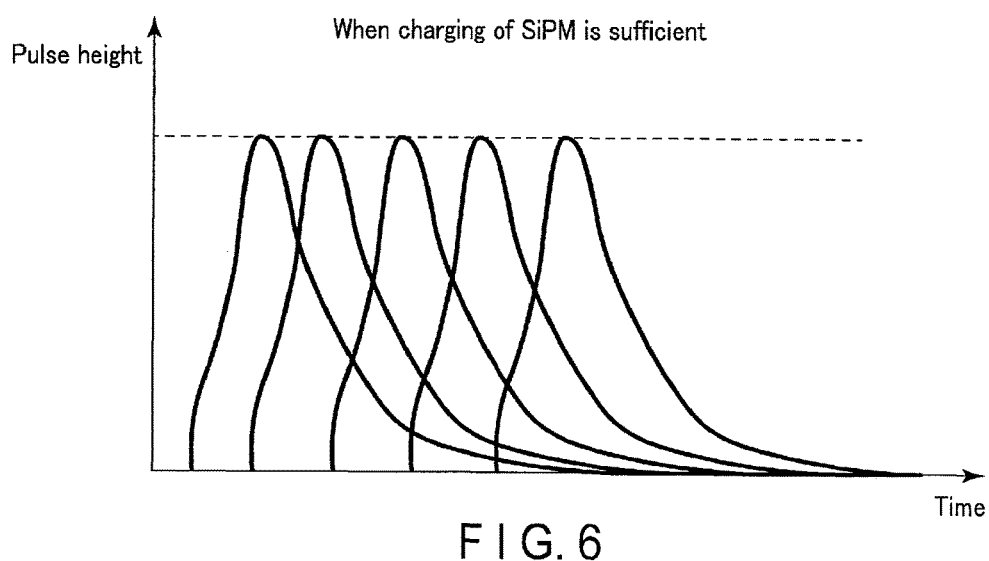
FIG. 6 is a graph showing the pulse height of a current pulse output from the detector pixel (SiPM) under a low dose.

The nonlinearity of the energy signal from the detector pixel 31 will be explained here. As described above, the APD cell 37 shifts to the charging period when it receives scintillation photons and ignites. Before the charging period is completed, the APD cell 37 cannot ignite or output only a current pulse of a low pulse height even if it receives scintillation photons. As shown in FIG. 6, under a low dose, the plurality of APD cells 37 included in the detector pixel 31 (SiPM) are sufficiently charged. Hence, when X-ray photons of the same energy enter, the pulse height of an energy signal caused by each X-ray photon is constant. As shown in FIG. 7, under a high dose, many APD cells 37 simultaneously ignite. For this reason, the detector pixel 31 (SiPM) is not sufficiently charged, and the pulse height of the energy signal becomes lower than the proper value. In this case, it is impossible to make discrimination between a pulse height caused by undercharging and a truly low pulse height. Hence, it cannot be said that the reliability of count data based on the energy signal, and thus, the reliability of the accuracy of energy resolution is high.

To improve the reliability of the accuracy of energy resolution under the high dose, the X-ray detection apparatus 15 according to this embodiment switches the count data generation mode between the charging period and the charging completion period of the plurality of APD cells 37.

Examples of the X-ray detection apparatus 15 according to this embodiment will be described below in detail. Note that the same reference numerals as in this embodiment denote constituent elements having almost the same functions in the following explanation, and a repetitive description will be made only when necessary.

EXAMPLE 1

Figure 8:
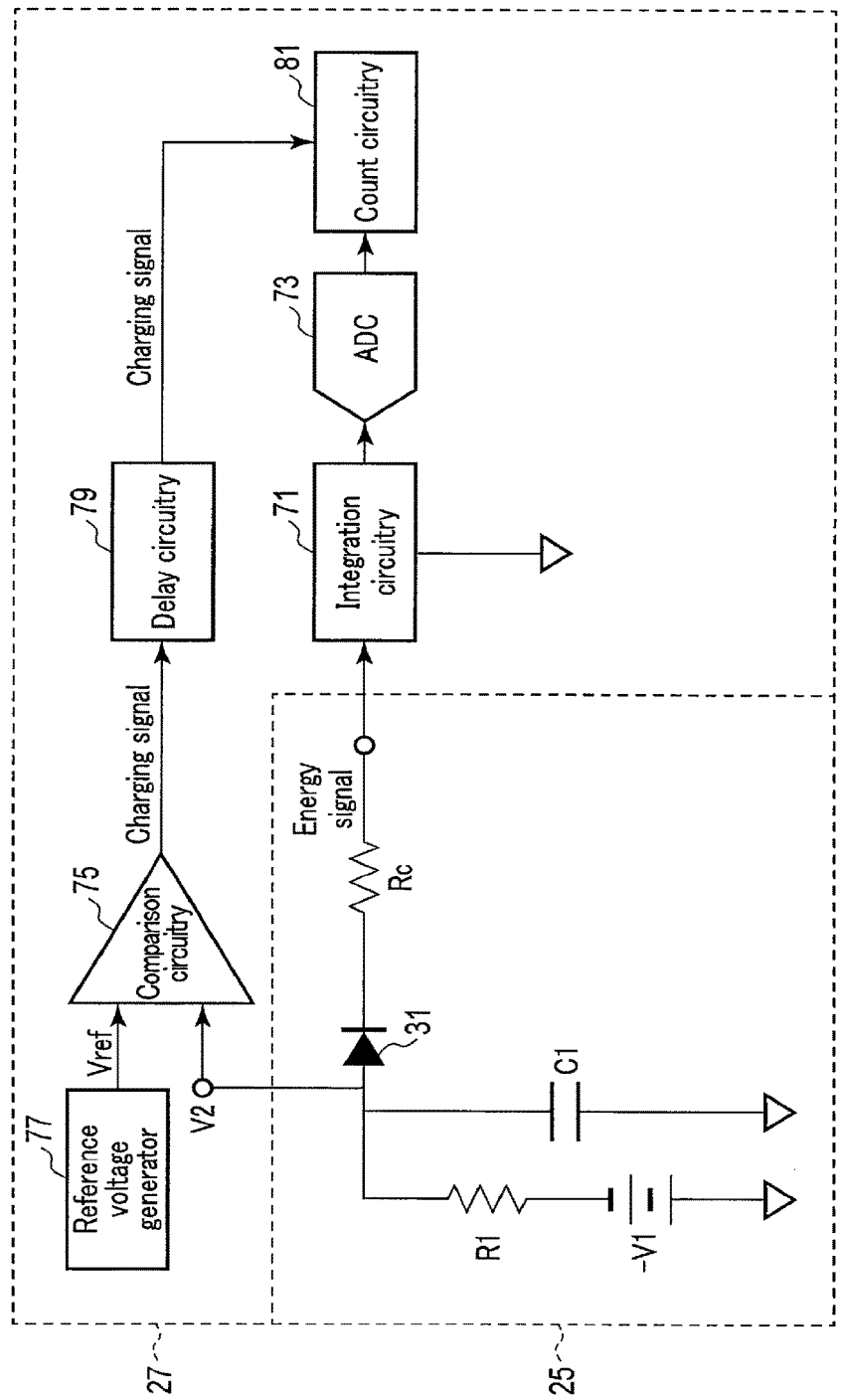
FIG. 8 is a block diagram showing the circuit arrangement of an X-ray detection apparatus according to Example 1 of the embodiment.

FIG. 8 is a block diagram showing the circuit arrangement of an X-ray detection apparatus 15 according to Example 1. The X-ray detection apparatus 15 includes read channels as many as detector pixels 31. The plurality of read channels are parallelly mounted on integrated circuitry such as an ASIC (Application Specific Integrated Circuit). The read channels have almost the same arrangement. For the descriptive convenience, FIG. 8 illustrates an arrangement corresponding to only one channel, and those for the remaining channels are not illustrated.

As shown in FIG. 8, the X-ray detection apparatus 15 includes an X-ray detector 25 and data acquisition circuitry 27. The X-ray detector 25 includes a detector pixel 31 in correspondence with each read channel. The detector pixel 31 receives X-ray photons and outputs an energy signal (current pulse) having a pulse height corresponding to the energy of the X-ray photons. The detector pixel 31 is connected to the data acquisition circuitry 27. The X-ray detector 25 includes not only the detector pixel 31 but also circuit elements such as a power supply V1, a wiring resistance R1, a capacitor C1 such as a parasitic capacitance or a bypass capacitor, and a quenching resistor Rc. The power supply V1 generates a reverse voltage to be applied to the detector pixel 31. The power supply V1 is connected to the anode side of the detector pixel 31 and, more specifically, the anode side of each of the plurality of APD cells included in the detector pixel 31. The reverse voltage can have any value and is set to, for example, about 80 V.

The data acquisition circuitry 27 counts the energy signal from the detector pixel 31, and generates, for each of a plurality of energy bins, count data representing the count of the incident X-ray photons based on the count of the energy signal. Upon counting the energy signal, the data acquisition circuitry 27 does not count the energy signal during the charging period of the detector pixel 31 but counts the energy signal during the charging completion period.

A detailed example of an arrangement for implementing the above function will be described. As shown in FIG. 8, the data acquisition circuitry 27 includes integration circuitry 71, an A/D converter (ADC) 73, comparison circuitry 75, reference voltage generator 77, delay circuitry 79, and count circuitry 81. The power supply V1 is multipoint-connected to the detector pixel 31 and the comparison circuitry 75. The output terminal of the detector pixel 31 is connected in series with the integration circuitry 71, the A/D converter 73, and the count circuitry 81 via a quenching resistor. The input terminals of the comparison circuitry 75 are connected to the power supply V1 and the reference voltage generator 77, and the output terminal is connected to the input terminal of the delay circuitry 79. The output terminal of the delay circuitry 79 is connected to the input terminal of the count circuitry 81.

The integration circuitry 71 integrates the analog energy signal from the detector pixel 31 over a minute time, and outputs an integrated energy signal. The output terminal of the integration circuitry 71 is connected to the input terminal of the A/D converter 73. The A/D converter 73 converts the integrated analog energy signal into a digital energy signal. The digital energy signal has a digital value corresponding to the pulse height of the integrated energy signal. The output terminal of the A/D converter 73 is connected to the input terminal of the count circuitry 81.

If the detector pixel 31 is in the charging period, the comparison circuitry 75 outputs an electrical signal (to be referred to as a charging signal hereinafter) representing that the detector pixel is in the charging period. If the detector pixel 31 is in the charging completion period, the comparison circuitry 75 does not output the charging signal. As shown in FIG. 8, the input terminals of the comparison circuitry 75 are connected to the output terminal of the reference voltage generator 77 and the anode side (input terminal) of the detector pixel 31. The reference voltage generator 77 generates a reference voltage Vref having the potential of the detector pixel 31 when it is in the steady state. The reference voltage Vref is input to the input terminal of the comparison circuitry 75. More specifically, the reference voltage Vref is set to almost the same potential as the applied voltage (reverse voltage) V1 to the detector pixel 31. A potential (to be referred to as a comparison voltage hereinafter) V2 on the anode side of the detector pixel 31 is also input to the input terminal of the comparison circuitry 75. The comparison circuitry 75 compares the comparison voltage V2 with the potential of the reference voltage Vref. If the comparison voltage V2 almost equals the potential of the reference voltage Vref, it means that the detector pixel 31 is in the steady state, and charging is completed. If the absolute value of the comparison voltage V2 is lower than that of the potential of the reference voltage Vref, it means that the detector pixel 31 is not in the steady state and is being charged. Hence, when the comparison voltage V2 almost equals the potential of the reference voltage Vref, the comparison circuitry 75 does not output the charging signal. When the absolute value of the comparison voltage V2 is lower than that of the potential of the reference voltage Vref, the comparison circuitry 75 outputs the charging signal. The charging signal is input to the input terminal of the delay circuitry 79. Note that the charging signal can be either a digital signal or an analog signal, and is assumed to be, for example, a digital signal to make a detailed description below.

The delay circuitry 79 is provided between the comparison circuitry 75 and the count circuitry 81. The delay circuitry 79 delays the input time of the charging signal to the count circuitry 81 to attain synchronization of input timing to the count circuitry 81 between the charging signal from the comparison circuitry 75 and the energy signal from the detector pixel 31. The delay time added to the charging signal by the delay circuitry 79 is, for example, the sum of the processing time of the integration circuitry 71 and that of the A/D converter 73. The output terminal of the delay circuitry 79 is connected to the input terminal of the count circuitry 81.

The count circuitry 81 counts the digital energy signal from the A/D converter 73 for each energy bin to which the pulse height of the energy signal belongs, and generates count data for each energy bin. For example, the count circuitry 81 is implemented by a histogram counter or an MCA (Multi-Channel Analyzer). Alternatively, the count circuitry 81 may be implemented by the count circuitry 81 of a signal channel and wave height discrimination circuitry parallelly implemented as many as the energy bins. The count circuitry 81 adds a flag to the energy signal input at almost the same time as the charging signal. This flag represents that the energy signal with the flag is derived from X-ray photons that have entered the detector pixel 31 in the charging period. The count circuitry 81 does not count an energy signal with the flag but counts an energy signal without the flag, thereby generating count data. The generated count data is transmitted to a console 50 via a noncontact data transmission apparatus or the like.

FIG. 9 is a timing chart of the X-ray detection apparatus 15 according to Example 1. As shown in FIG. 9, in a case in which the intensity of incident X-rays is lower than a predetermined value Ic corresponding to an excessive dose, even if X-ray photons enter the detector pixel 31, charging of the detector pixel 31 with the reverse voltage V1 is immediately completed, and therefore, the comparison voltage V2 does not lower from the steady state. However, when the intensity of the incident X-rays reaches the predetermined value Ic (time t1), charging of the detector pixel 31 with the reverse voltage V1 delays, and the comparison voltage V2 lowers from the steady state. The comparison circuitry 75 measures the comparison voltage V2, and measures the difference between the comparison voltage V2 and the potential of the reference voltage Vref. If the potential of the reference voltage Vref is different from the comparison voltage V2, that is, if the absolute value of the comparison voltage V2 is lower than that of the potential of the reference voltage Vref, the comparison circuitry 75 considers that the detector pixel 31 is in the charging period, and outputs the charging signal. The count circuitry 81 adds a flag to the energy signal input during the period when the charging signal is output. The energy signal with the flag is not counted by the count circuitry 81.

As shown in FIG. 9, when the intensity of the incident X-rays lowers and reaches the predetermined value Ic (time t2), charging of the detector pixel 31 with the reverse voltage V1 is completed, and the comparison voltage V2 matches the potential of the reverse voltage V1 again. If the reference voltage Vref is not different from the comparison voltage V2, that is, if the absolute value of the comparison voltage V2 is not lower than that of the reference voltage Vref, the comparison circuitry 75 considers that the detector pixel 31 is in the charging completion period, and does not output the charging signal. The count circuitry 81 does not add a flag to the energy signal input during the period when the charging signal is output. The energy signal without the flag is counted by the count circuitry 81.

According to Example 1 described above, if the absolute value of the comparison voltage V2 is lower than the steady state, the data acquisition circuitry 27 determines that the detector pixel is in the charging period. If the absolute value of the comparison voltage V2 is not lower than the steady state, the data acquisition circuitry 27 determines that the detector pixel is in the charging completion period. If the detector pixel 31 is in the charging period, the data acquisition circuitry 27 does not count the energy signal from the detector pixel 31. If the detector pixel 31 is in the charging completion period, the data acquisition circuitry 27 counts the energy signal from the detector pixel 31. Since energy signal from the detector pixel 31 during the charging period is not reflected on the count data, and only the energy signal from the detector pixel 31 during the charging completion period is reflected on the count data, the correctness of the count data improves. The reliability of the accuracy of energy resolution of the X-ray detection apparatus 15 thus improves.

Note that in the above description, a flag representing that an energy signal with the flag is derived from X-ray photons that have entered the detector pixel 31 in the charging period is added to the energy signal. However, the embodiment is not limited to this. That is, the embodiment is limited to the flag, or information of an arbitrary number of bits may be used if it represents that the energy signal with the flag is derived from X-ray photons that have entered the detector pixel 31 in the charging period.

Additionally, in the above description, the delay circuitry 79 is provided between the comparison circuitry 75 and the count circuitry 81. However, the embodiment is not limited to this. That is, if the charging signal and the digital signal can be synchronized without the delay circuitry 79, or they need not be synchronized, the delay circuitry 79 need not be provided.

EXAMPLE 2

In the X-ray detection apparatus 15 according to Example 1, to avoid the count circuitry 81 from counting the energy signal in the charging period, the comparison circuitry 75 determines the charging period and the charging completion period, and supplies, to the count circuitry 81, the charging signal representing that the detector pixel is in the charging period. An X-ray detection apparatus 15 according to Example 2 includes a switch between a detector pixel 31 and count circuitry 81 to disconnect the detector pixel 31 from the count circuitry 81 in the charging period. Note that the same reference numerals as in Example 1 denote constituent elements having almost the same functions in the following explanation, and a repetitive description will be made only when necessary.

FIG. 10 is a block diagram showing the circuit arrangement of the X-ray detection apparatus 15 according to Example 2. As shown in FIG. 10, in Example 2, the output terminal of the detector pixel 31 is connected in series with a switch 83, integration circuitry 71, an A/D converter 73, and the count circuitry 81 via a quenching resistor. The output terminal of comparison circuitry 75 is connected to the switch 83.

As in Example 1, if the detector pixel 31 is in the charging period, the comparison circuitry 75 outputs the charging signal. If the detector pixel 31 is in the charging completion period, the comparison circuitry 75 does not output the charging signal. The charging signal is supplied to the switch 83.

If the detector pixel 31 is in the charging period, the switch 83 disconnects an X-ray detector 25 from the count circuitry 81. If the detector pixel 31 is in the charging completion period, the switch 83 connects the X-ray detector 25 to the count circuitry 81. More specifically, during the period when the charging signal is output from the comparison circuitry 75, the switch 83 disconnects the X-ray detector 25 from the count circuitry 81. During the period when the charging signal is not output from the comparison circuitry 75, the switch 83 connects the X-ray detector 25 to the count circuitry 81.

FIG. 11 is a timing chart of the X-ray detection apparatus 15 according to Example 2. The ordinate of FIG. 11 defines an output value, and the abscissa defines time. As shown in FIG. 11, when an excessive amount of X-ray photons enters the detector pixel 31 under a high dose, an energy signal is output from the detector pixel 31 while a comparison voltage V2 lowers. The comparison circuitry 75 measures the comparison voltage V2, and measures the difference between a reference voltage Vref and the comparison voltage V2. If the potential of the reference voltage Vref is different from the comparison voltage V2, that is, if the absolute value of the comparison voltage V2 is lower than that of the potential of the reference voltage Vref, the comparison circuitry 75 considers that the detector pixel 31 is in the charging period, and outputs the charging signal. During the period when the charging signal is output, the switch 83 disconnects the detector pixel 31 from the integration circuitry 71. Accordingly, even if photons enter the detector pixel 31, the APD cells do not ignite, and therefore, the detector pixel 31 does not output an energy signal. That is, when the detector pixel 31 and the integration circuitry 71 are disconnected, the detector pixel 31 can continuously be charged without outputting an energy signal.

As shown in FIG. 11, when charging of the detector pixel 31 with a reverse voltage V1 continues, the charging is completed, and the comparison voltage V2 matches the potential of the reverse voltage V1 again (time t2). If the potential of the reference voltage Vref is not different from the comparison voltage V2, that is, if the absolute value of the comparison voltage V2 is not lower than that of the potential of the reference voltage Vref, the comparison circuitry 75 considers that the detector pixel 31 is in the charging completion period, and does not output the charging signal. During the period when the charging signal is not output, the switch 83 connects the detector pixel 31 to the integration circuitry 71. Accordingly, if photons enter the detector pixel 31, the APD cells ignite, and therefore, the detector pixel 31 outputs an energy signal. That is, when the detector pixel 31 and the integration circuitry 71 are connected, the energy signal is supplied to the subsequent stage of the detector pixel 31. As a result, the energy signal (digital signal) derived from the X-ray photons that have entered during the period when the charging signal is not output is counted by the count circuitry 81.

According to Example 2, if the detector pixel 31 is in the charging period, the data acquisition circuitry 27 does not count the energy signal from the detector pixel 31, as in Example 1. If the detector pixel 31 is in the charging completion period, the data acquisition circuitry 27 counts the energy signal from the detector pixel 31. Since only the energy signal derived from X-ray photons that have entered the detector pixel 31 during the charging completion period is reflected on count data, the correctness of the count data improves. The reliability of the accuracy of energy resolution of the X-ray detection apparatus 15 thus improves.

Also, according to Example 2, when the detector pixel 31 is in the charging period, the data acquisition circuitry 27 disconnects an detector pixel 31 from the count circuitry 81. When the detector pixel 31 is in the charging completion period, the data acquisition circuitry 27 connects the detector pixel 31 to the count circuitry 81. During the period when the detector pixel 31 is disconnected from the count circuitry 81, even if X-ray photons enter, the comparison voltage V2 does not lower, and charging of the detector pixel 31 continues. That is, a dead time is forcibly generated in the detector pixel 31 by disconnecting it from the count circuitry 81, thereby shortening the charging period of the detector pixel 31. Hence, the X-ray detection apparatus 15 according to Example 2 can efficiently use X-ray irradiation, as compared to Example 1.

EXAMPLE 3

The X-ray detection apparatus 15 according to each of Examples 1 and 2 is provided with the comparison circuitry 75 that compares the potential of the reference voltage Vref with a comparison voltage V2 to determine the charging period and the charging completion period. An X-ray detection apparatus 15 according to Example 3 determines the charging period and the charging completion period using a charging time decided in advance. Note that the same reference numerals as in Example 1 or 2 denote constituent elements having almost the same functions in the following explanation, and a repetitive description will be made only when necessary.

FIG. 12 is a block diagram showing the circuit arrangement of the X-ray detection apparatus 15 according to Example 3. As shown in FIG. 12, in Example 3, the output terminal of a detector pixel 31 is multipoint-connected to a switch 83 and pulse detection circuitry 85 via a quenching resistor Rc. One output system includes the switch 83, integration circuitry 71, an A/D converter 73, and count circuitry 81 which are connected in series. The other output system includes the pulse detection circuitry 85 and time determination circuitry 87 which are connected in series. The output terminal of the time determination circuitry 87 is connected to the input terminal of the switch 83. One input terminal of the time determination circuitry 87 is connected to the output terminal of the pulse detection circuitry 85, and the other input terminal is connected to the output terminal of charging time storage circuitry 89.

The pulse detection circuitry 85 detects the energy signal from the detector pixel 31. More specifically, the pulse detection circuitry 85 measures the pulse height of the energy signal from the detector pixel 31. If the measured pulse height is equal to or larger than a predetermined value, the pulse detection circuitry 85 outputs a signal (to be referred to as a detection signal hereinafter) representing that the energy signal is detected. If the measured pulse height is not equal to or larger than the predetermined value, the pulse detection circuitry 85 does not output the detection signal. The predetermined value can be set to an arbitrary value. Since the pulse detection circuitry 85 aims at detecting only the presence/absence of the energy signal, the predetermined value may be set to zero or the like. The detection signal is supplied to the time determination circuitry 87. Note that the detection signal can be implemented by either an analog signal or a digital signal, and is assumed to be, for example, a digital signal to make a detailed description below.

Based on the elapsed time from the output of the energy signal from the detector pixel 31, the time determination circuitry 87 determines whether the detector pixel 31 is in the charging period or in the charging completion period. The time determination circuitry 87 is implemented by counter circuitry that counts a clock pulse by a high-speed clock. The clock frequency of the time determination circuitry 87 is preferably as high as possible. The clock frequency is preferably ten or more times higher than the maximum count rate of the photon counting circuitry system (the integration circuitry 71, the A/D converter 73, and the count circuitry 81). More specifically, when the pulse detection circuitry 85 defects the energy signal, that is, upon receiving the detection signal supplied from the pulse detection circuitry 85, the time determination circuitry 87 measures the elapsed time from the point of time when the energy signal is detected. The time determination circuitry 87 compares the elapsed time with a predetermined charging time. If the elapsed time does not exceed the predetermined charging time, the time determination circuitry 87 determines that the pixel 31 is in the charging period. If the elapsed time exceeds the charging time, the time determination circuitry 87 determines that the detector pixel 31 is in the charging completion period. The charging time is stored in the charging time storage circuitry 89. Upon determining that the detector pixel 31 is in the charging period, the time determination circuitry 87 outputs the charging signal to the switch 83. Upon determining that the detector pixel 31 is in the charging completion period, the time determination circuitry 87 does not output the charging signal to the switch 83.

The charging time storage circuitry 89 stores the charging time to be compared with the elapsed time. The charging time storage circuitry 89 is implemented by, for example, a storage device such as a ROM. Physically, the charging time varies between the plurality of detector pixels 31. However, the time constant needed for charging of the detector pixel 31 is decided based on the product of a wiring resistance R1 and a capacitor C1. For this reason, by measuring the wiring resistance R1 and the capacitor C1 of each detector pixel 31 in advance, the charging time of the detector pixel 31 can be measured or calculated. The charging time storage circuitry 89 stores the charging time of the detector pixel 31 connected to the read channel to which the charging time storage circuitry 89 belongs. The stored charging time is read out by the time determination circuitry 87.

FIG. 13 is a timing chart of the X-ray detection apparatus according to Example 3. The ordinate of FIG. 13 defines an output value, and the abscissa defines time. As shown in FIG. 13, when an excessive amount of X-ray photons enters the detector pixel under a high dose (time t1), an energy signal is output from the detector pixel 31 with lowering of the comparison voltage V2. The pulse detection circuitry 85 detects the energy signal output from the detector pixel 31 and outputs a detection signal. Upon receiving the detection signal, the time determination circuitry 87 measures the elapsed time from the input of the detection signal, and compares the measured elapsed time with the charging time. Upon determining that the elapsed time does not exceed the charging time, the time determination circuitry 87 considers that the detector pixel 31 is in the charging period, and outputs the charging signal. During the period when the charging signal is output, the switch 83 disconnects the detector pixel 31 from the integration circuitry 71. Accordingly, even if X-ray photons enter the detector pixel 31, the APD cells do not ignite, and therefore, the detector pixel 31 does not output an energy signal. That is, when the detector pixel 31 and the integration circuitry 71 are disconnected, the detector pixel 31 can continuously be charged without outputting an energy signal.

As shown in FIG. 13, upon determining that the elapsed time exceeds the charging time (time t2), the time determination circuitry 87 considers that the detector pixel 31 is in the charging completion period, and does not output the charging signal. During the period when the charging signal is not output, the switch 83 connects the detector pixel 31 to the integration circuitry 71. Accordingly, if X-ray photons enter the detector pixel 31, the APD cells ignite, and therefore, the detector pixel 31 outputs an energy signal. That is, when the detector pixel 31 and the integration circuitry 71 are connected, the energy signal is supplied to the subsequent stage of the detector pixel 31. As a result, the energy signal derived from the X-ray photons that have entered during the period when the charging signal is not output is counted.

As described above, if the detector pixel 31 is in the charging period, the data acquisition circuitry 27 according to Example 3 does not count the energy signal from the detector pixel 31, as in Examples 1 and 2. If the detector pixel 31 is in the charging completion period, the data acquisition circuitry 27 counts the energy signal from the detector pixel 31. Since only the energy signal from the detector pixel 31 during the charging completion period is reflected on count data, the correctness of the count data improves. The reliability of the accuracy of energy resolution of the X-ray detection apparatus 15 thus improves.

Also, the data acquisition circuitry 27 according to Example 3 can determine the charging period and the charging completion period using the charging time decided in advance without including the comparison circuitry needed in the data acquisition circuitry 27 according to Examples 1 and 2 to determine the charging period and the charging completion period. For this reason, in Example 3, since high voltage circuitry necessary to generate the reference voltage need not be included, the circuit scale can be reduced as compared to Examples 1 and 2.

EXAMPLE 4

The X-ray detection apparatus 15 according to each of Examples 1, 2 and 3 does not count an energy signal derived from X-ray photons that have entered during the charging period but counts an energy signal derived from X-ray photons that have entered during the charging completion period. An X-ray detection apparatus 15 according to Example 4 corrects an energy signal derived from X-ray photons that have entered during the charging period based on the relationship between an amplification factor and an applied voltage to a detector pixel 31. The same reference numerals as in Example 1, 2, or 3 denote constituent elements having almost the same functions, and a repetitive description will be made only when necessary.

Figure 14:
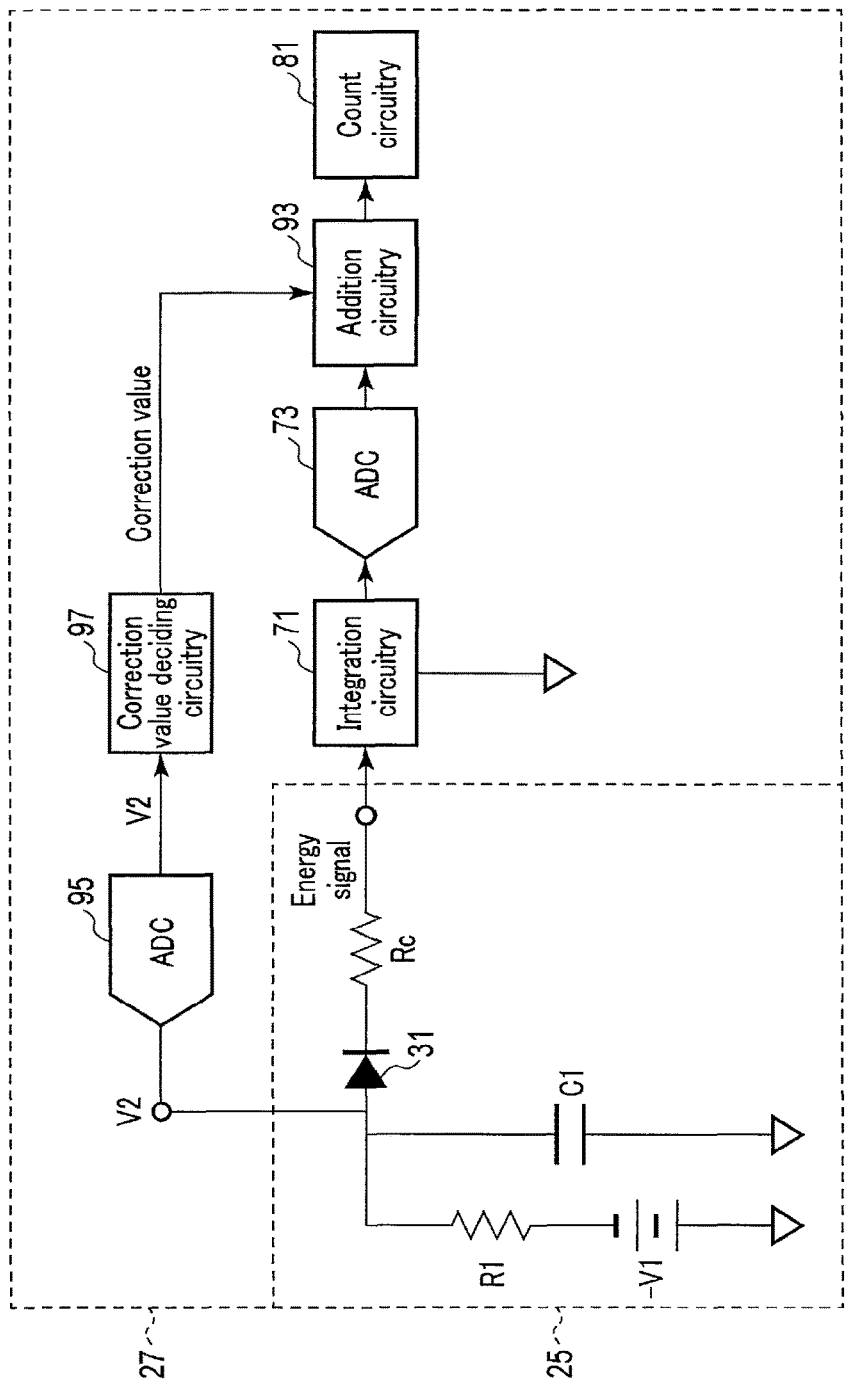
FIG. 14 is a block diagram showing the circuit arrangement of an X-ray detection apparatus according to Example 4 of the embodiment.

FIG. 14 is a block diagram showing the circuit arrangement of the X-ray detection apparatus 15 according to Example 4. As shown in FIG. 14, in Example 4, a power supply V1 is multipoint-connected to the detector pixel 31 and an A/D converter 95. The output terminal of the detector pixel 31 is connected in series with integration circuitry 71, an A/D converter 73, addition circuitry 93, and count circuitry 81. The input terminal of the A/D converter 95 is connected to the anode side of the detector pixel 31. The A/D converter 95 and correction value deciding circuitry 97 are connected in series. The output terminal of the correction value deciding circuitry 97 is connected to an input terminal of the addition circuitry 93.

The A/D converter 95 measures a comparison voltage V2 of the detector pixel 31 in real time, and converts an analog signal representing the measured comparison voltage V2 into a digital signal.

The correction value deciding circuitry 97 determines a correction value for the pulse height of an energy signal based on the digital comparison voltage V2. More specifically, the correction value deciding circuitry 97 stores an LUT (Lookup Table) representing the relationship between the measured comparison voltage V2 and the correction value for the pulse height of an energy signal. The correction value deciding circuitry 97 inputs the measured comparison voltage V2 to the LUT, and outputs a digital signal (to be referred to as a correction value signal hereinafter) concerning a correction value corresponding to the comparison voltage V2. The output correction value signal is input to the addition circuitry 93. Note that if the comparison voltage V2 equals the potential of the reverse voltage V1, a correction value signal having a correction value equal to zero is output. That is, if the comparison voltage V2 equals the potential of the reverse voltage V1, the energy signal from the A/D converter 73 is not corrected.

The addition circuitry 93 adds the correction value represented by the correction value signal from the correction value deciding circuitry 97 to the pulse height of the energy signal from the A/D converter 73, and outputs an energy signal having the corrected pulse height. The corrected pulse height equals the pulse height of an energy signal derived from incident X-ray photons in a case in which the comparison voltage V2 of the detector pixel 31 equals the comparison voltage V2 (the potential of the reverse voltage V1) in the charging completion period.

The count circuitry 81 counts the corrected energy signal from the addition circuitry 93, and acquires count data for each of a plurality of energy bins.

Correction value deciding processing by the correction value deciding circuitry 97 will be described below. FIG. 15 is a graph showing the linear relationship between the reverse voltage and the amplification factor of the detector pixel 31. The ordinate of FIG. 15 defines the amplification factor, and the abscissa defines the reverse bias voltage. As shown in FIG. 15, a linear relationship holds between the amplification factor and the bias reverse voltage. The amplification factor almost linearly rises as the reverse bias voltage rises.

The correction value for the pulse height is determined in accordance with the linear relationship between the reverse voltage and the amplification factor of each detector pixel 31. The linear relationship between the reverse voltage and the amplification factor changes between APD cells. The linear relationship between the reverse voltage and the amplification factor of each of a plurality of APD cells included in the detector pixel 31 is measured, and the linear relationship between the reverse voltage and the amplification factor concerning the detector pixel 31 is decided based on a plurality of measured linear relationships corresponding to the plurality of APD cells. Alternatively, a representative linear relationship in the plurality of APD cells included in the detector pixel 31 may be decided as the linear relationship concerning the detector pixel 31.

Let H0 be the pulse height in a case in which an APD cell is completely charged, h0 be the pulse height in a case in which the APD cell is insufficiently charged, and A be the attenuation ratio from H0 to h0. Based on the pulse height H0 and the attenuation ratio A, the pulse height h0 is defined by $$h0 = A * H0 \ (0 < A \leq 1) \quad (1)$$

The attenuation ratio A is uniquely determined based on an amplification factor K1 for the applied voltage V1 and an amplification factor K2 for the comparison voltage V2. The relationship between the amplification factor K1 for the applied voltage V1, the amplification factor K2 for the comparison voltage V2, the pulse height H0 for the applied voltage V1, and the pulse height h0 for the comparison voltage V2 is defined by $$H0 : h0 = K1 : K2 = K1 : K1 - (V1 - V2) * \alpha$$

$$H0 = K1 / (K1 - (V1 - V2) * \alpha) * h \quad (2)$$

where $\alpha$ is the slope of a line representing the change in the amplification factor corresponding to the change in the reverse voltage shown in FIG. 15.

A correction value B is determined based on the pulse height H0 and the pulse height h0, as indicated by $$B = H0 - h0 \qquad (3)$$
$$= (V1 - V2) * \alpha / (K1 - (V1 - V2) * \alpha) * h0$$

The correction value B is calculated in advance for each comparison voltage V2, and the relationship between each comparison voltage V2 and the correction value B is defined by the LUT.

As described above, when the comparison voltage V2 is input from the A/D converter, the correction value deciding circuitry determines the correction value B corresponding to the comparison voltage V2 from the LUT. The correction value signal concerning the determined correction value B is supplied to the addition circuitry 93. After the correction value signal is input, the addition circuitry 93 adds the correction value represented by the correction value signal to the digital value of the digital signal input from the A/D converter, thereby calculating the corrected pulse height. The digital signal concerning the corrected pulse height is supplied to the count circuitry. The count circuitry 81 counts the digital signal concerning the corrected pulse height.

As described above, data acquisition circuitry 27 according to Example 4 corrects the pulse height of an energy signal derived from X-ray photons that have entered the detector pixel 31 during the charging period using the relationship between the reverse voltage and the amplification factor of the detector pixel 31, thereby estimating the pulse height of an energy signal that can be obtained when the X-ray photons enter the detector pixel 31 during the charging completion period. Hence, the X-ray detection apparatus according to Example 4 can increase the X-ray use efficiency, in other words, can improve the number of samples of a count, as compared to Examples 1, 2, and 3.

As described above, the data acquisition circuitry 27 according to Example 4 generates corrected count data for each energy bin from count data derived from X-ray photons that have entered during the charging period. The corrected count data estimates the count in a case in which the X-ray photons that have entered during the charging period are assumed to enter during the charging completion period. Image reconstruction circuitry 51 generates a photon counting CT image based on the corrected count data. In photon counting imaging, X-rays of a high dose enter the X-ray detection apparatus 15 for a thin body part such as a lung field or a child. According to Example 4, the above-described arrangement allows the X-ray photons that have entered during the charging period to contribute to the photon counting CT image. It is therefore possible to improve the contrast of a thin body part in the image.

EXAMPLE 5

The X-ray detection apparatus 15 according to Example 4 includes the addition circuitry 93 to correct an energy signal. An X-ray detection apparatus 15 according to Example 5 includes multiplication circuitry 99 to correct an energy signal. The same reference numerals as in Example 4 denote constituent elements having almost the same functions in the following explanation, and a repetitive description will be made only when necessary.

FIG. 16 is a block diagram showing the circuit arrangement of the X-ray detection apparatus 15 according to Example 5. As shown in FIG. 16, an input terminal of the multiplication circuitry 99 is connected to the output terminal of an A/D converter 73. The input terminal of count circuitry 81 is connected to the output terminal of the multiplication circuitry 99. The input terminal of correction value deciding circuitry 98 is connected to the output terminal of an A/D converter 95. The output terminal of the correction value deciding circuitry 98 is connected to the other input terminal of the multiplication circuitry 99. The correction value deciding circuitry 98 calculates K1/(K1−(V1−V2)*α) of equations (2), that is, the reciprocal of an attenuation ratio A as a correction value C. As described above, the attenuation ratio A is uniquely determined based on an amplification factor K1 for an applied voltage V1 and an amplification factor K2 for a voltage V2. Upon receiving the comparison voltage V2 from the A/D converter 95, the correction value deciding circuitry 98 determines the correction value C corresponding to the comparison voltage V2 based on the attenuation ratio A, and outputs a correction value signal concerning the correction value C.

The multiplication circuitry 99 multiplies the pulse height of the energy signal from the A/D converter 73 by the correction value C represented by the correction value signal from the correction value deciding circuitry 98, and outputs an energy signal having the corrected pulse height. The corrected pulse height equals the pulse height of an energy signal derived from incident X-ray photons in a case in which the comparison voltage V2 of the detector pixel 31 equals the comparison voltage V2 (the potential of the reverse voltage V1) in the charging completion period.

The count circuitry 81 counts the corrected energy signal from the multiplication circuitry 99, and acquires count data for each of a plurality of energy bins.

As described above, data acquisition circuitry 27 according to Example 5 corrects the pulse height of an energy signal derived from X-ray photons that have entered the detector pixel 31 during the charging period using the relationship between the reverse voltage and the amplification factor of the detector pixel 31, thereby estimating the pulse height of an energy signal that can be obtained when the X-ray photons enter the detector pixel 31 during the charging completion period. Hence, the X-ray detection apparatus according to Example 5 can increase the X-ray use efficiency, in other words, can improve the number of samples of a count, as compared to Examples 1, 2, and 3.

In addition, the correction value C according to Example 5 is simpler than the correction value B according to Example 4 as can be seen from comparison of equations (2) and (3). Hence, according to Example 5, it is possible to more easily correct the energy signal.

(Modifications)

In the above embodiment, the photon counting imaging apparatus is assumed to be an X-ray CT type apparatus (photon counting CT apparatus). However, the photon counting imaging apparatus according to the embodiment may be an X-ray imaging type apparatus (photon counting XR apparatus).

In this case, the photon counting XR apparatus includes an arm to which the X-ray tube 13 and the X-ray detection apparatus 15 are attached, and a support frame that supports the arm movably with respect to a plurality of moving axes, in place of the rotation frame 11. The support frame incorporates the rotation actuator 21, and is actuated by the gantry control circuitry 23.

The X-ray detection apparatus 15 in the photon counting XR apparatus is almost the same as the X-ray detection apparatus 15 in the photon counting CT apparatus, and a description thereof will be omitted.

According to the arrangement, even in the photon counting XR apparatus, the data acquisition circuitry 27 can switch the count data generation mode between the charging period and the charging completion period of the detector pixel, as in the photon counting CT apparatus.

(Summary)

As described above, the photon counting imaging apparatus according to the embodiment includes the X-ray tube 13, the X-ray detector 25, and the data acquisition circuitry 27. The X-ray tube 13 generates X-rays. The X-ray detector 25 includes the scintillator 33 configured to convert the X-rays generated by the X-ray tube 13 into scintillation, the detector pixel 31 including the plurality of APD cells 37 each configured to individually generate an electrical signal of a predetermined pulse height in response to the scintillation, and the output circuitry 39 configured to generate an energy signal having a pulse height corresponding to the energy of incident X-ray photons based on the electrical signals from the plurality of APD cells 37. The data acquisition circuitry 27 generates count data representing the count of X-rays for each energy bin based on the energy signal. The data acquisition circuitry 27 switches the count data generation mode between the charging period and the charging completion period of the detector pixel 31.

With the above-described arrangement, the photon counting imaging apparatus according to this embodiment does not count the energy signal from the detector pixel 31 in a case in which the detector pixel 31 is in the charging period, and counts the energy signal from the detector pixel 31 in a case in which the detector pixel 31 is in the charging completion period. Since only the energy signal from the detector pixel 31 during the charging completion period is reflected on count data, the correctness of the count data improves. The reliability of the accuracy of energy resolution of the X-ray detection apparatus 15 thus improves.

In photon counting imaging, X-rays of a high dose enter the X-ray detection apparatus 15 for a lung field or a child. According to this embodiment, the above-described arrangement can prevent degradation of the count caused by the high dose. It is therefore possible to improve the energy resolution of the X-ray detection apparatus 15 in a high dose and thus reconstruct a high-resolution image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A photon counting imaging apparatus comprising:
an X-ray tube configured to generate X-rays;
an X-ray detector including a phosphor configured to convert the X-rays generated by the X-ray tube into scintillation, a detector pixel including a plurality of photoelectric conversion cells each configured to individually generate an electrical signal of a predetermined pulse height in response to the scintillation, and output circuitry configured to generate an energy signal having a pulse height corresponding to energy of the X-rays based on the electrical signals from the plurality of photoelectric conversion cells; and
data acquisition circuitry configured to generate count data representing a count of the X-rays for each energy band based on the energy signal, the data acquisition circuitry correcting the energy signal based on a relationship between an amplification factor and an applied voltage to the detector pixel during a period until the voltage applied to the detector pixel recovers from a breakdown voltage to a reverse bias voltage.

2. The apparatus of claim 1, wherein the data acquisition circuitry comprises:
correction value deciding circuitry configured to determine a correction value according to the relationship between the amplification factor and the applied voltage to the detector pixel about the pulse height of the energy signal;
correction circuitry configured to correct the pulse height of the energy signal based on the correction value and outputs a corrected signal; and
count circuitry configured to count the corrected signal from the correction circuitry.

3. A photon counting imaging apparatus comprising:
an X-ray tube configured to generate X-rays;
an X-ray detector including a phosphor configured to convert the X-rays generated by the X-ray tube into scintillation, a detector pixel including a plurality of photoelectric conversion cells each configured to individually generate an electrical signal of a predetermined pulse height in response to the scintillation, and output circuitry configured to generate an energy signal having a pulse height corresponding to energy of the X-rays based on the electrical signals from the plurality of photoelectric conversion cells;
count circuitry configured to count the energy signal from the X-ray detector and generate count data; and
a connector configured to electrically connect the X-ray detector and the count circuitry, the connector disconnecting the X-ray detector from the count circuitry during a charging period until a voltage applied to the detector pixel recovers from a breakdown voltage to a reverse bias voltage.

4. The apparatus of claim 3, further comprising a comparator configured to compare a measured potential of the detector pixel with a reference potential, output a charging signal representing the charging period to the connector when the absolute value of measured potential is lower than the absolute value of the reference potential, and not output the charging signal when the absolute value of measured potential is not lower than the absolute value of the reference potential,
wherein the connector disconnects the X-ray detector from the count circuitry when the charging signal is supplied, and connects the X-ray detector to the count circuitry when the charging signal is not supplied.

5. The apparatus of claim 3, further comprising determination circuitry configured to determine the charging period and a charging completion period based on an elapsed time from output of the energy signal, upon determining the charging period, output a charging signal representing the charging period to the connector, and upon determining the charging completion period, not output the charging signal to the connector,
wherein the connector disconnects the X-ray detector from the count circuitry when the charging signal is supplied, and connects the X-ray detector to the count circuitry when the charging signal is not supplied.

6. The apparatus of claim 5, further comprising detection circuitry configured to detect the energy signal from the X-ray detector,
   wherein the determination circuitry measures the elapsed time when the energy signal is detected by the detection circuitry, outputs the charging signal to the connector until the elapsed time exceeds a charging time of charges corresponding to the photoelectric conversion cell, and does not output the charging signal to the connector when the elapsed time exceeds the charging time.

7. An X-ray detection apparatus comprising:
   an X-ray detector including a phosphor configured to convert X-rays into scintillation, a detector pixel including a plurality of photoelectric conversion cells each configured to individually generate an electrical signal of a predetermined pulse height in response to the scintillation, and output circuitry configured to generate an energy signal having a pulse height corresponding to energy of the X-rays based on the electrical signals from the plurality of photoelectric conversion cells; and
   data acquisition circuitry configured to generate count data representing a count of the X-rays for each energy band based on the energy signal from the X-ray detector, the data acquisition circuitry switching a count data generation form between a charging period and a charging completion period of the detector pixel.

* * * * *